(12) United States Patent
Small et al.

(10) Patent No.: US 10,973,855 B2
(45) Date of Patent: Apr. 13, 2021

(54) METHODS FOR TREATING MACULAR DEGENERATION

(71) Applicant: Kent W. Small, Glendale, CA (US)

(72) Inventors: Kent W. Small, Glendale, CA (US); Edwin M. Stone, Iowa City, IA (US)

( * ) Notice: Subject to any disclaimer, the term of this patent is extended or adjusted under 35 U.S.C. 154(b) by 261 days.

(21) Appl. No.: 15/729,583

(22) Filed: Oct. 10, 2017

(65) Prior Publication Data
US 2018/0117091 A1      May 3, 2018

Related U.S. Application Data

(60) Provisional application No. 62/406,316, filed on Oct. 10, 2016.

(51) Int. Cl.
| | |
|---|---|
| *C12Q 1/68* | (2018.01) |
| *A61K 35/30* | (2015.01) |
| *C12Q 1/6883* | (2018.01) |
| *A61P 27/02* | (2006.01) |

(52) U.S. Cl.
CPC .............. *A61K 35/30* (2013.01); *A61P 27/02* (2018.01); *C12Q 1/6883* (2013.01); *C12Q 2600/156* (2013.01)

(58) Field of Classification Search
None
See application file for complete search history.

(56) References Cited

PUBLICATIONS

Small (Ophthalmology Jan. 2016 vol. 123 pp. 9-18).*
GRCh37-hg19-Genome -Assembly-NCBI Webpages—Feb. 10, 2020—5 pp.*

* cited by examiner

*Primary Examiner* — James Martinell
(74) *Attorney, Agent, or Firm* — Adriano & Associates

(57) ABSTRACT

The present invention relates to compositions and methods for treating, screening and diagnosing macular degeneration in a subject. This is a new pathway found which is the only one known to be involved in development of the human macula. Manipulation and control of this pathway will allow rebuilding and/or repair of the macula, making new and improved better maculae.

9 Claims, 21 Drawing Sheets
Specification includes a Sequence Listing.

Figure 1. A – I

Family B

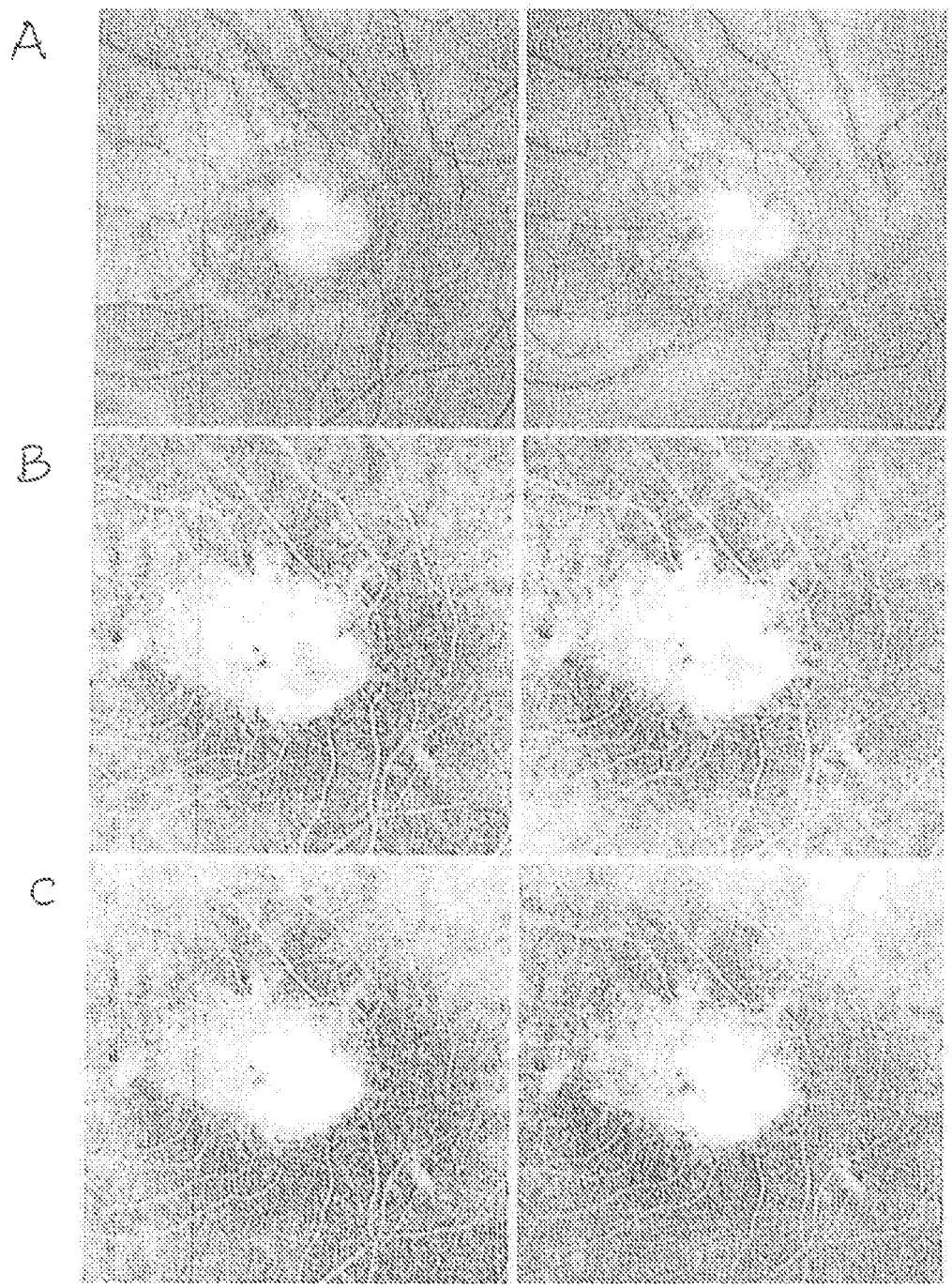
Figure 5A-C

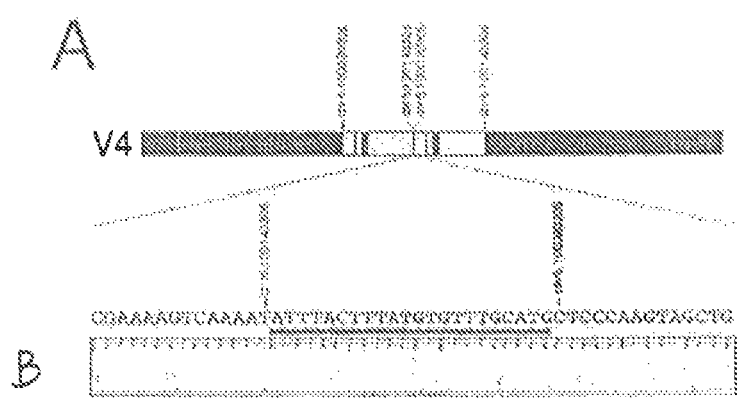
Figure 6A-B

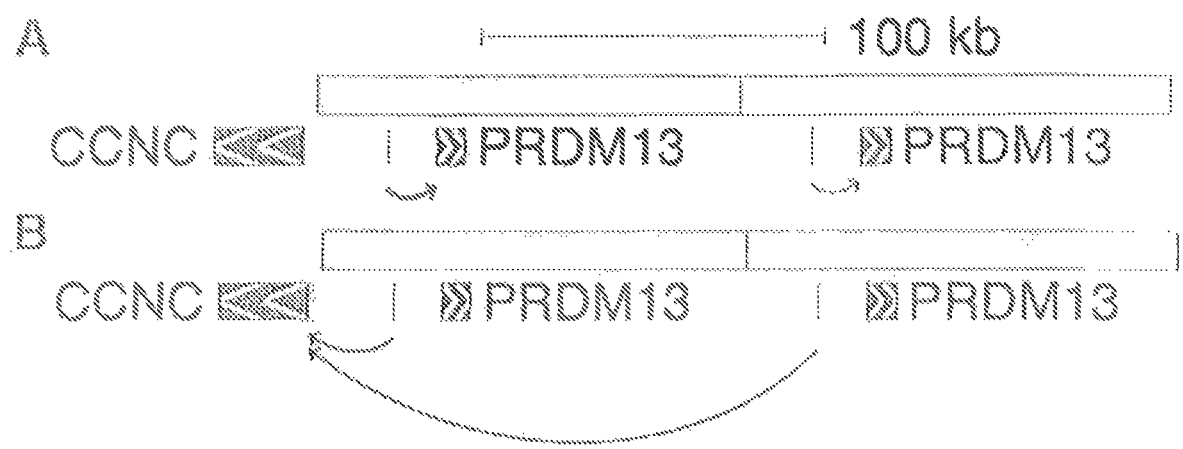
Figure 7A-B

Figure 8

CAGAATGTGCAAGTGCTGAAACTTCTGATTGTGTACATTTACTGATGT
CCCACTGACCAAACAAGTCAATGGCAAAGCTTAAGATCATTATGAAAG
GAGATCATGCAAGAGCATGAATACCAGGACATGTTCAATTCACTGGGAGATGA
TGAATGTACACAGTTTGCTACCAGGAAATTAACCCAGGAAGAGAGAAAAACA
ATCACTGGAAAAATTATGTGGAAATCAAAAGAGCATTATTTTTTGCAAT
ATTAC

Figure 9A-C

A. *HCMD V1 family – G to T transversion mutation at chr6:100849266* variant V1 (chr6:100,849,366-100,849,926): CTGCTTGTCTCACATTTACTTATGTCCCGCTGACCAGAGCA wild-type (chr6:100,849,886-100,849,926): CTGCTTGTCTCACATTTACTGATGTCCCGCTGACCAGAGCA B. *HCMD V2 family – G to C transversion mutation at chr6:100841907* variant V2 (chr6:100,849,867-100,841,907): ATGCAAGAGCATGAATACCAgGAGTTCAATTCACTGGGCGA wild-type (chr6:100,849,867-100,841,907): ATGCAAGAGCATGAATACCAgGAGTTCAATTCACTGGGCGA C. *HCMD V3 family – A to T transition mutation at chr6:100841940* variant V3 (chr6:100,841,920-100,841,960): AGTTTGCTACAGGAAATTAAtCCAGAAGAGAAAAAACA wild-type (chr6:100,841,920-100,841,960): AGTTTGCTACAGGAAATTAAaCCAGAAGAGAAAAAACA

Figure 10A-B a. Duplicated minor/in sequences (Chr6:180,819,305-180,929,404) at proximal end of the 123,101-bp tandem duplication (Chr6:180,819,205-180,943,306) in NCI&D V4 family CTCCCAAGTAGCTGGGATTACAGATGTGCCACCATGCCCAGGATAATTT
TCTTTTTTTTTTTCTCTCTTGGATTTTGAGTAGAGATGGGGTTTCACCA
TGTTGGTCAGGCTGGTCTGGAAACTCCTGACCTCAGTTGATCCACCCACCT
CAGCCTCCCAAAGTGCTGGGATTATAGGCCTGAGCCACCGTGCCCGGCCA b. Duplicated nucleotide sequences (Chr6: 180,143, 167-180, 143, 306) at distal end of the 123,101-bp tandem duplication (Chr6: 180,819,205-180, 943, 306) in NCI&D V4 family TATCTTACACTCTCAAACAATCTTAAACTTTCAAAACTGAAATTA
TATCAGTATCTCTCTGACCACAATGAAATAAGACTAGATGTCAGTAAC
AAGAGACATTTTGGAACTGGACATACACATGAAATTACACAATGCT
CCTGAATGAACAGTGTCCAAAACGAATTAAGAAGGAAATTCAAAAT

SEQUENCE LISTING

<160> NUMBER OF SEQ ID NOS: 37

<210> SEQ ID NO 1

```
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: DNA insertion associated with PRDM13 gene
      duplication Human Chromosome 6

<400> SEQUENCE: 1
atttacttta tgtgtttgca tg                                              22

<210> SEQ ID NO 2
<211> LENGTH: 50
<212> TYPE: DNA
<213> ORGANISM: Homo sapiens
<220> FEATURE:
<221> NAME/KEY: misc_feature
<222> LOCATION: (1)..(50)
<223> OTHER INFORMATION: Junction sequence between duplicated PRDM13
      gene repeats on chromosome 6

<400> SEQUENCE: 2
ggaaaagtca aaatatttac tttatgtgtt tgcatgctcc caagtagctg                 50

<210> SEQ ID NO 3
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: DNA insertion associated with IRX1 gene
      duplication on Human chromosome 5

<400> SEQUENCE: 3
ctgagaattc ataat                                                      15

<210> SEQ ID NO 4
<211> LENGTH: 51
<212> TYPE: DNA
<213> ORGANISM: Homo sapiens
<220> FEATURE:
<221> NAME/KEY: misc_feature
<222> LOCATION: (1)..(51)
<223> OTHER INFORMATION: Junction sequence between Duplicated IRX1 gene
      repeats on chromosome 5

<400> SEQUENCE: 4
tttaattcat aatgactgag aattcataat gactgagaag aggaacttcc c               51

<210> SEQ ID NO 5
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Forward Primer for chr6_100040343-100040606

<400> SEQUENCE: 5
gcattcccta aagcacttga cc                                              22

<210> SEQ ID NO 6
<211> LENGTH: 23
<212> TYPE: DNA
<213> ORGANISM: Homo sapiens
<220> FEATURE:
<221> NAME/KEY: misc_feature
```

```
<222> LOCATION: (1)..(23)
<223> OTHER INFORMATION: Reverse Primer chr6_100040343-1000040606

<400> SEQUENCE: 6
gatagctacc cctcctctga atg                                            23

<210> SEQ ID NO 7
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Forward Primer for chr6_100040524-100040879

<400> SEQUENCE: 7
ctgatcattt gaatcaaggc ag                                             22

<210> SEQ ID NO 8
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Reverse Primer for chr6_100040524-100040879

<400> SEQUENCE: 8
cagcacttgc acatttgtgt c                                              21

<210> SEQ ID NO 9
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: Forward Primer for chr6_100040803-100041001

<400> SEQUENCE: 9
gagaagacta gatcaggctt cttc                                           24

<210> SEQ ID NO 10
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Reverse Primer for chr6_100040803-100041001

<400> SEQUENCE: 10
ctctcattct ctgattttta c                                              21

<210> SEQ ID NO 11
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: Forward Primer for chr6_100041063-100041470

<400> SEQUENCE: 11
cactggaaaa attatgtgga aatc                                           24

<210> SEQ ID NO 12
```

```
<211> LENGTH: 26
<212> TYPE: DNA
<213> ORGANISM: Homo sapiens
<220> FEATURE:
<221> NAME/KEY: misc_feature
<222> LOCATION: (1)..(26)
<223> OTHER INFORMATION: Reverse Primer for chr6_100041063-100041470

<400> SEQUENCE: 12
gagtaattaa tgaagttgac aagttg                                    26

<210> SEQ ID NO 13
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Forward Primer chr6_100041063-100041470

<400> SEQUENCE: 13
gataaatcat atcttagacc gc                                        22

<210> SEQ ID NO 14
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: Reverse Primer for chr6_100041063-100041470

<400> SEQUENCE: 14
ctcatgccta taatccccag cac                                       23

<210> SEQ ID NO 15
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Forward Primer for chr5_Junction Fragment

<400> SEQUENCE: 15
gttttcacga aagtgcaaag g                                         21

<210> SEQ ID NO 16
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Reverse Primer for chr5_Junction Fragment

<400> SEQUENCE: 16
ggggtggaag agaagagagg                                           20

<210> SEQ ID NO 17
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Forward Primer for PRDM13 Exon 3 to Exon 4

<400> SEQUENCE: 17
```
ggaggagctg acagtgtggt                                                    20

<210> SEQ ID NO 18
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Reverse Primer for PRDM13 Exon 3 to Exon 4

<400> SEQUENCE: 18
aaacgtcctc cagcagtacc ag                                                 22

<210> SEQ ID NO 19
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Forward Primer for IRX1 Exon 3 to Exon 4

<400> SEQUENCE: 19
cagcagttaa agtcgccctt                                                    20

<210> SEQ ID NO 20
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: Reverse Primer for IRX1 Exon 3 to Exon 4

<400> SEQUENCE: 20
aaaagtaaaa gaagacccTt aa                                                 22

<210> SEQ ID NO 21
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: Forward Primer for CCNC Exon 8 to Exon 9

<400> SEQUENCE: 21
cttgatagtg tatcatcctt ata                                                23

<210> SEQ ID NO 22
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: Reverse Primer for CCNC Exon 8 to Exon 9

<400> SEQUENCE: 22
tcattcacta tcctccatgc aagg                                               24

<210> SEQ ID NO 23
<211> LENGTH: 20
<212> TYPE: DNA
<213> ORGANISM: Homo sapiens
<220> FEATURE:

<221> NAME/KEY: misc_feature
<222> LOCATION: (1)..(20)
<223> OTHER INFORMATION: Forward Primer for PAX6 Exon 5 to Exon 7

<400> SEQUENCE: 23
ccggcagaag attgtagagc                                          20

<210> SEQ ID NO 24
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Reverse Primer for PAX6 Exon 5 to Exon 7

<400> SEQUENCE: 24
gcccgttcaa catccttagt                                          20

<210> SEQ ID NO 25
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: Forward Primer for RHO Exon 2 to Exon 5

<400> SEQUENCE: 25
gggagaacca tgccatcat                                           19

<210> SEQ ID NO 26
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: Reverse Primer for RHO Exon 2 to Exon 5

<400> SEQUENCE: 26
tcgtctccgt cttggacac                                           19

<210> SEQ ID NO 27
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Forward Primer for S-Opsin Exon 1 to Exon 2

<400> SEQUENCE: 27
cgccagctgt gaacggatac t                                        21

<210> SEQ ID NO 28
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Reverse Primer for S-Opsin Exon 1 to Exon 2

<400> SEQUENCE: 28
ccaataccaa tggtccaggt                                          20

```
<210> SEQ ID NO 29
<211> LENGTH: 256
<212> TYPE: DNA
<213> ORGANISM: Homo sapiens
<220> FEATURE:
<221> NAME/KEY: misc_feature
<222> LOCATION: (1)..(256)
<223> OTHER INFORMATION: DNase I hypersensitive site upstream of human
      PRDM13 gene

<400> SEQUENCE: 29
cacaaatgtg caagtgctga aacttctgct tgtgtcacat ttactgatgt cccactgacc     60
agagcaagtc atatggcaaa gcttaagatc attatgaaag gagattatgc aagagcatga    120
aataccagga ggttcaattc actggggatg attatgtaac agtttgctac aggaaattaa    180
ccccagaaga gagaaaaaac aatcactgga aaaattatgt ggaaatcaaa agagccatta    240
tttttggcaa tattac                                                   256

<210> SEQ ID NO 30
<211> LENGTH: 41
<212> TYPE: DNA
<213> ORGANISM: Homo sapiens
<220> FEATURE:
<221> NAME/KEY: misc_feature
<222> LOCATION: (1)..(41)
<223> OTHER INFORMATION: NCMD variant V1 (chr6:100,040886-100,040,926)

<400> SEQUENCE: 30
ctgcttgtgt cacatttact tatgtcccac tgaccagagc a                         41

<210> SEQ ID NO 31
<211> LENGTH: 41
<212> TYPE: DNA
<213> ORGANISM: Homo sapiens
<220> FEATURE:
<221> NAME/KEY: misc_feature
<222> LOCATION: (1)..(42)
<223> OTHER INFORMATION: Wild-type (chr6:100,040886-100,040,926)

<400> SEQUENCE: 31
ctgcttgtgt cacatttact gatgtcccac tgaccagagc a                         41

<210> SEQ ID NO 32
<211> LENGTH: 41
<212> TYPE: DNA
<213> ORGANISM: Homo sapiens
<220> FEATURE:
<221> NAME/KEY: misc_feature
<222> LOCATION: (1)..(41)
<223> OTHER INFORMATION: NCMD variant V2 (chr6:100,040,968-100,041,007)

<400> SEQUENCE: 32
atgcaagagc atgaatacca cgaggttcaa ttcactgggg a                         41

<210> SEQ ID NO 33
<211> LENGTH: 41
<212> TYPE: DNA
<213> ORGANISM: Homo sapiens
<220> FEATURE:
<221> NAME/KEY: misc_feature
<222> LOCATION: (1)..(41)
<223> OTHER INFORMATION: Wild-type (chr6:100,040,967-100,041,007)

<400> SEQUENCE: 33
atgcaagagc atgaatacca ggaggttcaa ttcactgggg a                         41
```

```
<210> SEQ ID NO 34
<211> LENGTH: 41
<212> TYPE: DNA
<213> ORGANISM: Homo sapiens
<220> FEATURE:
<221> NAME/KEY: misc_feature
<222> LOCATION: (1)..(41)
<223> OTHER INFORMATION: NCMD variant v3 (chr6:100,041020-100,041,060)

<400> SEQUENCE: 34
agtttgctac aggaaaataa tcccagaaga gagaaaaaac a                            41

<210> SEQ ID NO 35
<211> LENGTH: 41
<212> TYPE: DNA
<213> ORGANISM: Homo sapiens
<220> FEATURE:
<221> NAME/KEY: misc_feature
<222> LOCATION: (1)..(41)
<223> OTHER INFORMATION: Wild-type (chr6:100,041,020-100,041,060)

<400> SEQUENCE: 35
agtttgctac aggaaattaa ccccagaaga gagaaaaaac a                            41

<210> SEQ ID NO 36
<211> LENGTH: 199
<212> TYPE: DNA
<213> ORGANISM: Homo sapiens
<220> FEATURE:
<221> NAME/KEY: misc_feature
<222> LOCATION: (1)..(199)
<223> OTHER INFORMATION: Duplicated nucleotide sequence
      (chr6:100,020,205-100,020,404) at proximal end of the 123-kb
      tandem duplication in NCMD V4 family

<400> SEQUENCE: 36
ctccaagtag ctgggattac aggtgcctgc caccatgccc agataatttt tttttttttt        60 ttttttttt ggattttag tagagatggg gtttcaccat gttggtcagg ctggtcacaa         120
actcctgacc tcagttaatc cacccacctc agcctcccaa agtgctggga ttataggcat       180
gagccaccgt gccccgcaa                                                    199

<210> SEQ ID NO 37
<211> LENGTH: 200
<212> TYPE: DNA
<213> ORGANISM: Homo sapiens
<220> FEATURE:
<221> NAME/KEY: misc_feature
<222> LOCATION: (1)..(200)
<223> OTHER INFORMATION: Duplicated nucleotide sequence
      (Chr:100,143,107-100,143,306) at distal end of 123-kb tandem
      duplication in NCMD V4 family

<400> SEQUENCE: 37
tatcttagac cgcaaaacaa gtcttaaaaa cgtttgaaaa aactgaaatt atatcaagta        60
cttctctgac cacaatgaaa taagactaga tgtcagtaac aagagacatt ttggaaacta      120
tacatacaca tggaaattac acaatatgct cctgaatgaa cagtatgtca atgaagaaat      180
taagaaggaa aagtcaaaat                                                   200
```

METHODS FOR TREATING MACULAR DEGENERATION

Throughout this application various publications are referenced. The disclosures of these publications in their entireties are hereby incorporated by reference into this application in order to more fully describe the state of the art to which this invention pertains.

BACKGROUND OF THE INVENTION

Few tissues in the human body are as important to the wellbeing of a person as the central 3 mm of the human retina. The ability to drive a car, recognize friends in public, and see words on a computer, cell phone or printed page are just a few of the many activities of daily living that depend heavily on the normal function of the macula. Only primates have maculae and this is a major distinguishing feature for human and primate visual function.

For all but a few people, the macula functions very well for the first 6 or 7 decades of life, but in older individuals, the macula is prone to a genetically and mechanistically diverse group of disorders that are known collectively as age-related macular degeneration (AMD). For many years, the neovascular complications of AMD were the most common cause of irreversible blindness in developed countries.[1-4] However, the recent advent of anti-vascular endothelial growth factor drugs[5-8] has dramatically reduced vision loss from neovascularization, thereby increasing the fraction of blindness caused by geographic atrophy of the macula.

There are at least 2 approaches that one could envision for reducing the burden of blindness caused by geographic atrophy of the macula. The first would be to understand the pathophysiologic mechanisms of AMD in sufficient detail that one could detect the disease at a very early stage, perhaps even as an asymptomatic genetic predisposition, and deliver a safe and effective preventive therapy to those at risk, much as statins are now used to reduce the risk of heart disease. Another strategy would be to rebuild an injured macula with new stem cell-derived retinal cells.[9, 10] Molecular genetics will play an important role in both of these approaches.

In the 1990s, scientists sought the genetic causes of several Mendelian forms of human macular disease for at least 2 reasons. First, it was possible that mild mutations in the genes responsible for these early-onset conditions might prove to be responsible for a significant subset of the age-related forms of the disease. Second, it was thought that by discovering how relatively minor alterations of individual genes could cause clinical findings similar to AMD, one would gain valuable insight into the normal function of the macula. Twenty years later, it is clear that none of the genes that cause the classic Mendelian macular dystrophies cause a significant fraction of the late-onset disease, and none of the genes that have been shown to predispose people to typical AMD cause any meaningful fraction of early-onset Mendelian macular disease.

The first of the classic macular dystrophies to have its gene mapped to a chromosome,[11] North Carolina macular degeneration (NCMD), is one of the last to have its specific disease-causing mutations identified. The reason for this delay—the unusual developmental mechanism of this disease—may ultimately make NCMD the most relevant of the Mendelian macular dystrophies to the treatment of AMD and other macular diseases. North Carolina macular degeneration was first described in a large kindred from North Carolina by Lefler et al[12] and later described in more detail by Frank et al.[13] The cross-sectional nature of these studies led the investigators to believe that the disease was slowly progressive. However, Small[14] reexamined the original Lefler kindred approximately 20 years later and realized that NCMD is in fact a nonprogressive developmental disorder with highly variable expressivity.

In the decades since the MCDR1 locus was mapped by Small et al., many additional families were found (most by Small et al.) worldwide with NCMD have been described,[15-20] including 1 family that links to a separate locus on chromosome 5 (MCDR3).[21,22] The critical region on chromosome 6 has been considerably narrowed to 856 kb by Small et al,[23,24] and all of the coding regions of genes within this interval have been exhaustively studied by us and other investigators.[25] The failure of these experiments to identify plausible disease-causing mutations in any of these kindreds suggested that the mutations were likely to exist in nonexomic DNA and to affect the expression of a nearby gene or genes rather than the structure of its gene product. The purpose of this study was to take advantage of recent advances in whole-genome sequencing to comprehensively screen the nonexomic sequences within the MCDR1 and MCDR3 loci to identify disease-causing mutations in families affected with these diseases.

SUMMARY OF INVENTION

The present invention relates to compositions and methods for treating, screening and diagnosing macular degeneration in a subject. This is a new pathway found which is the only one known to be involved in development of the human macula. Manipulation and control of this pathway will allow rebuilding and/or repair of the macula, making new and improved better maculae.

In one embodiment, the invention provides a method for treating macular degeneration comprising: obtaining a biological sample from the subject with macular degeneration; determining presence of a mutation in a nuclease, e.g., DNase1, hypersensitive region or a transcriptional regulatory region of a retinal transcription factor gene, PRDM13 gene; and administering a retinal cell, a progenitor cell or a pluripotent stem cell lacking the mutation in the eye of the subject so as to form part or all of a macula lutea in the subject, thereby treating macular degeneration in a subject.

The invention further provides a method for restoring a macula lutea in a subject with macular degeneration comprising: obtaining a biological sample from the subject with macular degeneration; determining presence of a mutation in a nuclease, e.g., DNase1, hypersensitive region or a transcriptional regulatory region of a gene associated with macula lutea development; and administering in the eye of the subject a retinal cell, a progenitor cell or a pluripotent stem cell lacking the mutation so as to form part or all of a macula lutea in the subject, thereby restoring a macula lutea in a subject with macular degeneration.

The invention additionally provides a method for preventing or reducing risk of macular degeneration in a subject comprising: obtaining a biological sample from the subject with macular degeneration; determining presence of a mutation in a nuclease hypersensitive region or a transcriptional regulatory region of a gene associated with macula lutea development; and administering a retinal cell, a progenitor cell or a pluripotent stem cell lacking the mutation so as to form part or all of a macula lutea in the subject, thereby preventing or reducing risk of macular degeneration in the subject.

Also, the invention provides a method for determining risk for developing macular degeneration in an embryo comprising obtaining a biological sample from the embryo; and determining presence of a mutation in a nuclease, e.g., DNase1, hypersensitive region or a transcriptional regulatory region of a gene associated with macular lutea development, wherein presence of said mutation is associated with macular degeneration, thereby determining risk for developing macular degeneration in the embryo.

Further, the invention provides a method for determining risk for developing macular degeneration in a fetus comprising obtaining a biological sample from the fetus; and determining presence of a mutation in a nuclease hypersensitive region or a transcriptional regulatory region of a gene associated with macular lutea development, wherein presence of said mutation is associated with macular degeneration, thereby determining risk for developing macular degeneration in the fetus.

The invention also provides a method for determining risk for developing macular degeneration in a subject comprising obtaining a biological sample from the subject; and determining presence of a mutation in a nuclease, e.g., DNase1, hypersensitive region or a transcriptional regulatory region of a gene associated with macular lutea development, wherein presence of said mutation is associated with macular degeneration, thereby determining risk for developing macular degeneration in the subject.

Kits comprising compositions of the invention (including retinal cells, progenitor cells or pluripotent stem cells described herein) for treating or diagnosing macular degeneration are also encompassed by the invention.

BRIEF DESCRIPTION OF THE FIGURES

FIG. 5A-C: Stereo images of panels B-D from FIG. 1.

FIG. 6A-B: Schematic illustration and chromatograms illustrating the breakpoints and regions of duplication in MCDR1 Family K (A).

FIG. 7A-B: Schematic illustration of the relative positions of the DNase hypersensitivity sites and the PRDM13 and CCNC genes in Family K.

FIG. 8: Nucleotide sequence of a 255-bp DNase hypersensitivity site (chr6:100040861-100041115) upstream of the PRDM13 gene as annotated in GRCh37/hg19 assembly of human genome (Genome Reference Consortium, Feb. 2009 release; see GenBank Accession Number: CM000668.1 for homo sapiens chromosome 6) which is found to be mutated in NCMD families (V1, V2 and V3) and is duplicated as part of 123,101-bp tandem duplication (chr6:100020205-100143306) for a NCMD family (V4).

FIG. 9A-C: Nucleotide change in the DNase I hypersensitive site upstream of PRDM13 gene in NCMD families (V1, V2 and V3) along with 20-nucleotide flanking sequence. Affected nucleotide is shown in small letter, bold and underlined. Chromosomal coordinates are in reference to GRCh37/hg19 assembly of human genome (Genome Reference Consortium, Feb. 2009 release, GRCh37 Genome Reference Consortium Human Reference 37 (GCA_000001405.1); see GenBank Accession Number: CM000668.1 for homo sapiens chromosome 6).

FIG. 10A-B: Duplicated nucleotide sequences at proximal and distal ends of the 123,101 bp tandem duplication (Chr6: 100,020,205-100,143,306) in NCMD V4 family.

DETAILED DESCRIPTION OF THE INVENTION

Definitions

Figure 1:
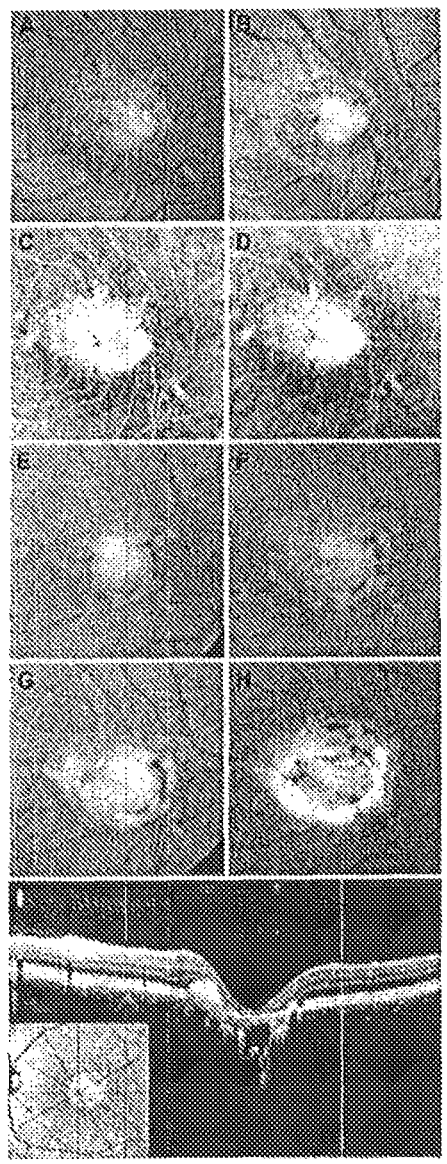
FIG. 1A-I: Retinal images spanning 30 years from the left eye of an affected member of family A: color fundus photograph (A), red-free fundus photograph (B), early-phase fluorescein angiogram (C), and late-phase fluorescein angiogram (D) at age 6 years; color fundus photographs at ages 8 years (E), 10 years (F), 11 years (G), and 33 years (H); optical coherence tomogram at age 33 years (I). This patient has been reported (Table 1). Stereo images of B-D are provided in FIG. 5A-C.

All scientific and technical terms used in this application have meanings commonly used in the art unless otherwise specified. As used in this application, the following words or phrases have the meanings specified.

As used herein, an "effective amount" refers to an amount effective, at dosages and for periods of time necessary, to achieve the desired therapeutic or prophylactic result.

As used herein, "treating" means using a therapy to ameliorate a disease or disorder (such as macular degeneration) or one or more of the biological manifestations of the disease or disorder; to alleviate one or more of the symptoms, effects or side effects associated with the disease or disorder or one or more of the symptoms or disorder or treatment thereof; or to slow the progression of the disease or disorder or one or more of the biological manifestations of the disease or disorder. Treatment includes eliciting a clinically significant response. For example, treatment of an eye condition may improve the symptoms of the condition, reduce the severity of a condition, alter the course of condition's progression and/or improve the basic condition. Throughout the specification, compositions of the invention and methods for the use thereof are provided and are chosen to provide suitable treatment for subjects in need thereof.

In order that the invention herein described may be more fully understood the following description is set forth.

The invention provides a method for treating macular degeneration in a subject. In one embodiment, the method comprises obtaining a biological sample from the subject with macular degeneration; determining presence of a mutation in a nuclease, e.g., DNase1, hypersensitive (i.e., methylation) region or a transcriptional regulatory region of a retinal transcription factor gene, e.g., a PRDM13 gene; and administering a retinal cell, a progenitor cell or a pluripotent stem cell lacking the mutation in, e.g., the eye of, the subject so as to form part or all of a macula lutea in the subject, thereby treating macular degeneration in a subject. In yet another embodiment, the method comprises obtaining a biological sample from the subject with macular degeneration; determining presence of a mutation in a nuclease, e.g., DNase1, hypersensitive (i.e., methylation) region or a transcriptional regulatory region of a retinal transcription factor gene, e.g., a PRDM13 gene; and manipulating the methylation binding of the DNase1 binding site so as to control the expression of PRDM13 and therefore treat macular diseases.

The invention additionally provides method for treating macular degeneration associated with overexpression of PRDM13 gene in a subject. In one embodiment, the method comprises administering a therapeutic agent to reduce the overexpression of the PRDM13 gene or normalize the expression of the PRDM13 gene, so as to inhibit macular degeneration or to restore macula lutea in the subject; thereby, treating macular degeneration associated with overexpression of PRDM13 gene in the subject. In another embodiment, the method comprises administering a therapeutic agent to reduce the overexpression of the PRDM13 gene or normalize the expression of the PRDM13 gene, so as to restore macula lutea in the subject; thereby, restoring macula lutea in the subject with macular degeneration associated with the overexpression of the PRDM13 gene.

An example of a therapeutic agent includes, but is not limited to, a polypeptide such as any of a methyl-CpG-binding domain, a bromodomain, a tandem PHD finger, a Pleckstrin homology (PH) domain, a Tudor domain, a WD40 domain, a chromodomain, a MBT (Malignant Brain Tumor) domain, a zf-CW (zinc finger CW) protein domain, a PWWP (proline-tryptophan-tryptophan-proline) domain, chromoshadow domain, 14.3.3 protein domain, BIR domain, or BCRT protein domain.

Another example therapeutic agent includes, but is not limited to, a gene editing agent such as a gene editing agent which is directed a non-coding region of a mutant PRDM13 gene associated with macular degeneration. In one embodiment, the gene editing agent may alter the sequence of the mutant PRDM13 gene so as to reduce the overexpression of the mutant PRDM13 gene.

The invention further provides a method for treating macular degeneration associated with a mutation in a nuclease hypersensitive region or a transcriptional regulatory region of a retinal transcription factor gene, PRDM13 gene in a subject. In one embodiment, the method comprises administering the cell(s) of the invention to a subject in a sufficient amount and under suitable conditions so that the isolated cell(s) exhibits functional integration (e.g. functional in vivo integration) and thereby treating the disorder. As used herein, "functional integration" includes integration by the cell(s) into, e.g., a local area of administration. For example, the cell suspension may be drawn up into a syringe and administered to anesthetized recipients. A single or multiple injections may be made using this procedure. In another embodiment, the method comprises obtaining a biological sample from the subject with macular degeneration; determining presence of a genetic change associated with macular lutea development; and administering a retinal cell, a progenitor cell or a pluripotent stem cell cured of the genetic change so as to form part or all of a macula lutea in the subject, thereby treating macular degeneration in the subject. In yet another embodiment, the macular degeneration is associated with a mutation in a nuclease hypersensitive region or a transcriptional regulatory region of a retinal transcription factor gene, PRDM13 gene and the method comprises administering to the subject a retinal cell, a progenitor cell or a pluripotent stem cell lacking the mutation so as to form part or all of a macula lutea in the subject, thereby treating macular degeneration in a subject.

Merely by way of example, the mutation may be a point mutation. The point mutation may be present in a subject, an embryo or a fetus. Further, in one embodiment, the point mutation is not found in non-affected subject without macular degeneration.

In one embodiment, the point mutation occurs in the nuclease hypersensitive region or transcriptional regulatory region between CCNC and PRDM13 genes. For example, the point mutation may occur in the nuclease, e.g., DNase1, hypersensitive region or transcriptional regulatory region upstream of a retinal transcription factor gene, PRDM13 gene. For example, the nuclease is DNase I. In an embodiment of the invention, the nuclease hypersensitive region may be a DNase I hypersensitive region.

In another embodiment, the point mutation occurs within a 255-bp DNase I hypersensitive region of human chromosome 6 at chromosomal location chr6:100040861-100041115 of the human genome (UCSC HG19 assembly, GRCh37 Genome Reference Consortium Human Reference 37 (GCA_000001405.1)).

In yet another embodiment, the mutation is a transversion mutation. For example, the transversion mutation may be a guanine to thymidine change at chromosomal location chr6:100040906 of the human genome or a guanine to cytosine change at chromosomal location chr6:100040987 of the human genome (UCSC HG19 assembly, GRCh37 Genome Reference Consortium Human Reference 37 (GCA_000001405.1)).

In a further embodiment, the mutation is a transition mutation. For example, the transition mutation may be a cytosine to thymine change at chromosomal location chr6:100041040 (UCSC HG19 assembly, GRCh37 Genome Reference Consortium Human Reference 37 (GCA_000001405.1)).

In yet a further embodiment, the mutation is a genetic change in a non-exomic region and not in a protein coding region, wherein the change is associated with macular degeneration.

In one embodiment of the invention, the genetic change is duplication of a chromosomal region associated with macular degeneration. For example, the duplication may be a tandem duplication of a 123-kb fragment on human chromosome 6. In an embodiment, the tandem duplication of a 123-kb fragment on human chromosome may be referred to as a 123,101 bp tandem duplication (Chr6:100,020,205-100,143,306). In one embodiment, the 123,101 bp tandem duplication (Chr6:100,020,205-100,143,306) is associated with a NCMD variant V4 family. In an embodiment, the tandem duplication has as a head-to-tail arrangement. Merely by way of example, the tandem duplication may comprise chromosomal DNA from location chr6:10002020205 to chr6:100143306 of the human genome (UCSC HG19 assembly, GRCh37 Genome Reference Consortium Human Reference 37 (GCA 000001405.1). Also, in another embodiment the tandem duplication additionally comprises an insertion of a 22-bp DNA sequence, ATTTACTT-TATGTGTTTGCATG (SEQ ID NO:1), into human chromosome 6. In yet another embodiment, the insertion is between the duplicated chromosomal DNA. In one example, the insertion between the duplicated chromosomal DNA may result in a new junction sequence: GGAAAAGT-CAAAATATTTACTTTACTTTATGTGTTTG-CATGCTCCCAAGTAGC TG (SEQ ID NO: 2). In yet a further embodiment, the duplication comprises duplication of PRDM13 gene on chromosome 6.

Additionally, in another embodiment, the duplication is a tandem duplication of a 898-kb DNA fragment on human chromosome 5. The tandem duplication may have a head-to-tail arrangement. In one embodiment of the invention, the tandem duplication comprises chromosomal DNA from location chr5:3587901 to chr5:4486027 of the human genome (UCSC HG19 assembly, GRCh37 Genome Reference Consortium Human Reference 37 (GCA_000001405.1). In yet a further embodiment, the tandem duplication additionally comprises an insertion of a 15-bp DNA sequence, CTGAGAATTCATAAT (SEQ ID NO:3), into human chromosome 5. For example, the insertion may be between the duplicated chromosomal DNA. In one embodiment, the insertion between the duplicated chromosomal DNA results in a new junction sequence:

TTTAATTCATAATGACTGAGAATTCATAATGACTGAGAAGAGGAACTTCC

C (SEQ ID NO: 4).

Sequence information and chromosomal location of nucleotide sequences and mutations are in reference to GRC37/hg19 assembly of the human genome of the Genome Reference Consortium Human Reference 37 (GCA_000001405.1) assembled February 2009. The sequences may be access through a web browser using Genome Browser developed and maintained by the Genome Bioinformatics Group, UCSC Genomics Institute of the University of California Santa Cruz.

The invention further provides a method for restoring a macula lutea in a subject with macular degeneration. In an embodiment of the invention, the method comprises obtaining a biological sample from the subject with macular degeneration; determining presence of a mutation in a nuclease hypersensitive region or a transcriptional regulatory region of a gene associated with macular lutea development; and administering in the eye of the subject a retinal cell, a progenitor cell or a pluripotent stem cell lacking the mutation so as to form part or all of a macula lutea in the subject, thereby restoring a macula lutea in a subject with macular degeneration.

In another embodiment, the method comprises obtaining a biological sample from the subject with macular degeneration; determining presence of a genetic change associated with macular lutea development; and administering a retinal cell, a progenitor cell or a pluripotent stem cell cured of the genetic change so as to form part or all of a macula lutea in the subject, thereby restoring a macula lutea in a subject with macular degeneration.

The invention additionally provides a method for preventing or reducing risk of macular degeneration in a subject comprising: obtaining a biological sample from the subject with macular degeneration; determining presence of a mutation in a nuclease hypersensitive region or a transcriptional regulatory region of a gene associated with macular lutea development; and administering a retinal cell, a progenitor cell or a pluripotent stem cell lacking the mutation so as to form part or all of a macula lutea in the subject, thereby preventing or reducing risk of macular degeneration in the subject.

Also, the invention provides a method for determining risk for developing macular degeneration in an embryo comprising obtaining a biological sample from the embryo and determining presence of a mutation in a nuclease hypersensitive region or a transcriptional regulatory region of a gene associated with macular lutea development, wherein presence of said mutation is associated with macular degeneration, thereby determining risk for developing macular degeneration in the embryo.

Further, the invention provides a method for determining risk for developing macular degeneration in a fetus comprising obtaining a biological sample from the fetus; and determining presence of a mutation in a nuclease hypersensitive region or a transcriptional regulatory region of a gene associated with macular lutea development, wherein presence of said mutation is associated with macular degeneration, thereby determining risk for developing macular degeneration in the fetus.

The invention also provides a method for determining risk for developing macular degeneration in a subject comprising obtaining a biological sample from the subject; and determining presence of a mutation in a nuclease hypersensitive region or a transcriptional regulatory region of a gene associated with macular lutea development, wherein presence of said mutation is associated with macular degeneration, thereby determining risk for developing macular degeneration in the subject.

Additionally, the invention also provides a method for preventing or reducing risk of macular degeneration in a subject comprising: obtaining a biological sample from the subject with macular degeneration; determining presence of a genetic change associated with macular lutea development; and administering a retinal cell, a progenitor cell or a pluripotent stem cell cured of the genetic change so as to form part or all of a macula lutea in the subject, thereby preventing or reducing risk of macular degeneration in the subject.

Further, the invention provides a method for determining risk for developing macular degeneration in an embryo comprising obtaining a biological sample from the embryo; and determining presence of a genetic change associated with macular lutea development, wherein presence of said genetic change is associated with macular degeneration, thereby determining risk for developing macular degeneration in the embryo.

Further still, the invention also provides a method for determining risk for developing macular degeneration in a fetus comprising obtaining a biological sample from the fetus; and determining presence of a genetic change associated with macular lutea development, wherein presence of said genetic change is associated with macular degeneration, thereby determining risk for developing macular degeneration in the fetus.

The invention additionally provides a method for determining risk for developing macular degeneration in a subject comprising obtaining a biological sample from the subject; and determining presence of a genetic change associated with macular lutea development, wherein presence of said genetic change is associated with macular degeneration, thereby determining risk for developing macular degeneration in the subject.

In accordance with the practice of the invention, the biological sample may comprise a cell from the subject, the embryo or the fetus. In one embodiment, the biological sample comprises a nucleic acid from said subject, said embryo or said fetus. Merely by way of example, the nucleic acid may comprise DNA, RNA or a combination thereof. The DNA may be genomic DNA or chromosomal DNA.

Further, in accordance with the practice of the invention, the macular degeneration may be a congenital disease. In another embodiment, the macular degeneration is age related. In yet another embodiment, the macular degeneration is a non-progressive disease. In a further embodiment, the macular degeneration is a progressive disease. In yet a further embodiment, the macular degeneration is North Carolina Macular Degeneration (NCMD). For example, the NCMD may be a mutation in the nonexomic region of human chromosome 6. In yet another embodiment, the macular degeneration is not a progressive macular degeneration). Further, in an embodiment of the invention, the macular degeneration is free of age-related macular degeneration, glaucoma, diabetic retinopathy and retinitis pigmentosa.

Also, in accordance with the practice of the invention, the retinal cell may be any of a photoreceptor cell, a non-photoreceptor neuron (e.g., amacrine) and a glial cell.

Examples of a photoreceptor cell includes any of a rod photoreceptor cell, a cone photoreceptor cell and a photosensitive retinal ganglion cell. Examples of a non-photoreceptor neuron includes any of a bipolar cell, a horizontal cell, an amacrine cell and a ganglion cell, a cuboidal cell, and a nerve cell. Examples of a glial cell include a Muller glial cell, an astroglial cell and a microglial cell.

In one embodiment of the invention, the retinal progenitor cell may be a multipotent cell which can give rise to all cells of the retina. Examples of cells of the retina include any of a retinal ganglion cell, an amacrine cell, a biopolar cell, a horizontal cell, a rod photoreceptor cell, a cone photoreceptor cell and a Muller glial cell.

In an embodiment of the invention, the pluripotent stem cell may be an induced pluripotent stem cell. In another embodiment, the retinal cell or the progenitor cell is derived from a pluripotent cell or induced pluripotent cell.

In accordance with the practice of the invention, the retinal cell, the progenitor cell or the pluripotent stem cell may be derived from the subject and may be genetically altered. For example, the genetic alteration may correct the mutation associated with the macular degeneration or compensates for dysregulated gene expression associated with the macular degeneration. In one embodiment, the dysregulated gene expression is expression of PRDM13 gene and/or its downstream target genes or expression of CCNC gene and/or its downstream target genes.

A "subject" may be a vertebrate, preferably a mammal, more preferably a human. Mammals include, but are not limited to, farm animals (such as cows, sheeps, and goats), sport animals, pets (such as cats, dogs and horses), primates (such as, monkeys, gorillas and chimpanzees), mice and rats. Additionally, in one embodiment, the subject is an embryo. Further, in accordance with the practice of the invention, the biological sample may be obtained by amniocentesis or from maternal blood or serum.

The invention further provides a method for diagnosing or classifying North Carolina Macular Degeneration in a subject comprising obtaining a biological sample from a subject; and determining presence of a genetic change selected from the group of: a guanine to thymidine change at chromosomal location chr6:100040906, a guanine to cytosine change at chromosomal location chr6:100040987, a cytosine to thymine change at chromosomal location chr:100041040, a 123-kb tandem duplication of chromosomal DNA on human chromosome 6 at location chr6:100020205-100143306, an insertion of a 22-bp DNA sequence, ATTTACTTTATGTGTTTGCATG (SEQ ID NO:1), between duplicated chr6:100020205-100143306 DNA on human chromosome 6, a 898-kb tandem duplication of chromosomal DNA on human chromosome 5 at location chr5:3587901-4486027, and an 15-bp DNA sequence, CTGAGAATTCATAAT (SEQ ID NO:3), between duplicated chr5:3587901-4486027 DNA on human chromosome 5; wherein presence of any said genetic change is associated with North Carolina Macular Degeneration, thereby diagnosing or classifying North Carolina Macular Degeneration in the subject.

Additionally provided by the invention is a composition for detection of North Carolina Macular Degeneration comprising a nucleic acid sequence or its complement comprising any of the nucleic acid sequence or portion thereof, for the variants provided in Table 1. See Supplemental FIG. 6A-C for sequence of variants provided in Table 1.

Also, the invention provides a method for treating or preventing North Carolina Macular Degeneration in a subject comprising administration of a therapeutic agent which reverses dysregulated gene expression associated with any of the nucleotide change as described in Table 1. In one embodiment, the therapeutic agent reverses dysregulation of PRDM13 gene expression involved in macular lutea development. For example, the therapeutic agent may comprise any one or more of a small molecule, a peptide, a protein, an antibody, a PRDM13 coding sequence, a binding partner or interacting protein for PRDM13, a nucleic acid, an siRNA, a micro RNA or a peptide-mimetic.

The invention additionally provides a method for recapitulating in vitro developmental defects of macula lutea associated with genetic variants of North Carolina Macular Degeneration mutations comprising: obtaining a fibroblast cell sample from a subject with North Carolina Macular Degeneration; reprogramming the fibroblast in (a) to obtain an induced pluripotent stem cell; culturing the induced pluripotent stem cell of (b) to obtain a population of induced pluripotent stem cells; and differentiating the induced pluripotent stem cells using a 3-dimensional differentiation protocol so as to undergo retinal development and form 3D eyecup.

Kits

According to another aspect of the invention, kits are provided. Kits according to the invention include package(s) or containers comprising the compositions of the invention (including retinal cells, progenitor cells or pluripotent stem cells described herein), defined culture medium and cell culture medium supplement. The kit may further include an instruction letter for the treatment and/or prophylaxis of a disease, for example, a veterinary disease.

The invention provides kits for growing and maintaining the compositions of the invention.

The phrase "package" means any vessel containing compositions (including stem cells, media, and/or media supplement) presented herein. In preferred embodiments, the package can be a box or wrapping. Packaging materials for use in packaging pharmaceutical products are well known to those of skill in the art. Examples of pharmaceutical packaging materials include, but are not limited to, tubes, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering compositions of the present invention to a subject having a condition in need of treatment. Kits may also comprise instructions for approved uses of compounds herein by regulatory agencies, such as the United States Food and Drug Administration. Kits may optionally contain labeling or product inserts for the present compositions. The package(s) and/or any product insert(s) may themselves be approved by regulatory agencies. The kits also can include buffers for preparing solutions for conducting the methods, and pipettes for transferring liquids from one container to another.

The following examples are provided to further illustrate aspects of the invention. These examples are non-limiting and should not be construed as limiting any aspect of the invention.

Example 1

Human Subjects

All subjects provided written informed consent for this research study, which was approved by the institutional review board of the University of Iowa and adhered to the tenets set forth in the Declaration of Helsinki. Blood samples were obtained from all subjects, and DNA was extracted using a nonorganic protocol, as previously described.[26]

Next-Generation Sequencing of MCDR1 Patients using BWA-mem, and single nucleotide variants and small insertions/deletions were identified using a GATK-based pipeline.[28, 29] Variants mapping outside the MCDR1-linked region and those found at a frequency of 1% or greater in public databases[30, 31, 32] were removed. Variants were then filtered, requiring that all affected individuals with a given haplotype share the heterozygous variant; all other individuals did not share the variant.

Copy number variants were investigated using Pindel and manual inspection of the aligned sequence data using the Integrative Genome Viewer.[33, 34] As a control, the identified genes were screened for copy number variants using Conifer[35] in an internal database of 953 whole exomes of patients with eye disease.

Confirmation of Whole-Genome Sequencing

Variants identified by whole-genome sequencing were confirmed using automated bidirectional DNA sequencing with dye termination chemistry on an ABI 3730 sequencer (ThermoFisher Scientific, Foster City, Calif.).

Screening of Control Subjects

A total of 261 normal control subjects were screened for the presence of V1 to V3 (Table 1) using unidirectional automated DNA sequencing. To evaluate these controls for the presence of V4 and V5 (Table 1), oligonucleotide primers were designed to amplify across the novel junctions created by these tandem duplications (Supplemental Table 1), and the products of these amplifications were evaluated by electrophoresis on 6% nondenaturing polyacrylamide gels followed by silver staining, as previously described.[36]

TABLE 1

Control Subjects Screened for the Presence of V1 to V3

| Family | Previously Published Family ID and Reference | Haplotype | Variant No. | HG19 Chromosomal Location | Nucleotide Change | No. Affected | No. Unaffected | No. Total Samples |
|---|---|---|---|---|---|---|---|---|
| A | 765[11, 14, 24, 40, 41, 42, 43, 44, 45] | North Carolina | V1 | chr6: 100040906 | G > T | 51 | 22 | 73 |
| B | 702[45] | North Carolina | V1 | chr6: 100040906 | G > T | 4 | 5 | 9 |
| C | 768[17, 24, 45] | North Carolina | V1 | chr6: 100040906 | G > T | 1 | 1 | 2 |
| D | 772[24, 45] | North Carolina | V1 | chr6: 100040906 | G > T | 4 | 0 | 4 |
| E | 1193[24, 45] | North Carolina | V1 | chr6: 100040906 | G > T | 3 | 0 | 3 |
| F | 1292[24, 45] | N/A | V1 | chr6: 100040906 | G > T | 2 | 1 | 3 |
| G | 769[16, 24, 45] | French | V2 | chr6: 100040987 | G > C | 1 | 0 | 1 |
| H | 718[45] | N/A | V2 | chr6: 100040987 | G > C | 1 | 0 | 1 |
| I | 1574 | N/A | V2 | chr6: 100040987 | G > C | 11 | 5 | 16 |
| J | 709[45] | N/A | V3 | chr6: 100041040 | C > T | 2 | 0 | 2 |
| K | 1463[19, 45] | Belize | V4 | chr6: 100020205-100143306 | 123101 bp tandem duplication | 11 | 4 | 15 | bp = base pairs; N/A = not available.

A targeted genome capture of the linked region was performed on 3 members of family A (2 affected and 1 unaffected), 2 members of family K, and 1 member of family B. Libraries prepared from these captures were sequenced on an Illumina HiSeq. In addition, 30_whole genomes were obtained from 5 affected individuals: 2 from family A, 1 from family K, and 2 from family L. These libraries were sequenced on an Illumina HiSeqX. All of these individuals are noted in blue in Supplemental FIG. 1A-L.

Bioinformatic Analysis of Next-Generation Sequencing Data

Sequences were analyzed as described previously.[27] Briefly, sequences were aligned to the reference genome See FIG. 9A-C for sequence of variants V1-V3 provided in Table 1 and FIG. 10 A-B for duplicated nucleotide sequences at proximal and distal ends the 123,101 bp tandem duplication (Chr6:100,020,205-100,143,306) in NCMD V4 family.

RNA Isolation and Reverse Transcription Polymerase Chain Reaction.

Total RNA was extracted from normal human iPSCs isolated at 0, 30, 60, and 100 days after differentiation using the RNeasy Mini-kit (Qiagen, Germantown, Md.), per the manufacturer's instructions, and 100 ng of RNA was amplified via SuperScript III One-Step RT-PCR System with Platinum Taq DNA Polymerase (Life Technologies) using the gene-specific primers described in Supplemental Table 1.

elsewhere.[11, 12, 13, 14, 16, 17, 19, 24, 40, 41, 42, 43, 44] Six of these families share a haplotype of short tandem-repeat polymor-

Supplemental Table 1 Oligonucleotide Primers

| Primer Name | Type | Sequence Description | Forward Sequence | Reverse Sequence |
|---|---|---|---|---|
| PRDM13-DHS_1 | S | chr6_100040343-100040606 | GCATTCCCTAAAGCACTTGACC (SEQ ID NO.: 5) | GATAGCTACCCCTCCTCTGAATG (SEQ ID NO.: 6) |
| PRDM13-DHS_2 | S | chr6_100040524-100040879 | CTGATCATTTGAATCAAGGCAG (SEQ ID NO.: 7) | CAGCACTTGCACATTTGTGTC (SEQ ID NO.: 8) |
| PRDM13-DHS_3* | S | chr6_100040803-100041001 | GAGAAGACTAGATCAGGCTTCTTC (SEQ ID NO.: 9) | CTCTCATTCTCTGATTTTTAC (SEQ ID NO.: 10) |
| PRDM13-DHS_5 | S | chr6_100041063-100041470 | CACTGGAAAAATTATGTGGAAATC (SEQ ID NO.: 11) | GAGTAATTAATGAAGTTGACAAGTTG (SEQ ID NO.: 12) |
| PRDM13_Duplication* | J | chr6_Junction Fragment | GATAAATCATATCTTAGACCGC (SEQ ID NO.: 13) | CTCATGCCTATAATCCCAGCAC (SEQ ID NO.: 14) |
| IRX1_Duplication* | J | chr5_Junction Fragment | GTTTTCACGAAAGTGCAAAGG (SEQ ID NO.: 15) | GGGGTGGAAGAGAAGAGAGG (SEQ ID NO.: 16) |
| PRDM13 | R | Exon 3 to Exon 4 | GGAGGAGCTGACAGTGTGGT (SEQ ID NO.: 17) | AAACGTCCTCCAGCAGTACCAG (SEQ ID NO.: 18) |
| IRX1 | R | Exon 3 to Exon 4 | CAGCAGTTAAAGTCGCCCTT (SEQ ID NO.: 19) | AAAAGTAAAAGAAGACCCTTAA (SEQ ID NO.: 20) |
| CCNC | R | Exon 8 to Exon 9 | CTTGATAGTGTATCATCCTTATA (SEQ ID NO.: 21) | TCATTCACTATCCTCCATGCAAGG (SEQ ID NO.: 22) |
| PAX6 | R | Exon 5 to Exon 7 | CCGGCAGAAGATTGTAGAGC (SEQ ID NO.: 23) | GCCCGTTCAACATCCTTAGT (SEQ ID NO.: 24) |
| RHO | R | Exon 2 to Exon 5 | GGGAGAACCATGCCATCAT (SEQ ID NO.: 25) | TCGTCTCCGTCTTGGACAC (SEQ ID NO.: 26) |
| S-Opsin | R | Exon 1 to Exon 2 | CGCCAGCTGTGAACGGATACT (SEQ ID NO.: 27) | CCAATACCAATGGTCCAGGT (SEQ ID NO.: 28) |

*Primers used to detect variants V1-V5
Oligo Type: S = sequencing amplification of genomic DNA, J = amplification spanning the 5' junction fragment, R = RT-PCR amplification from RNA Immunocytochemistry of 3-Dimensional Induced Pluripotent Stem Cell Derived Eyecups.

Three-dimensional iPSC-derived eyecups were embedded in 4% agarose, sectioned at a thickness of 100 μm using a Leica VT1000 S vibratome (Leica Microsystems, Wetzlar, Germany) and labeled with primary antibodies targeted against mouse anti-SOX2 (#MAB2018; 1:1000; R&D Systems, Minneapolis, Minn.), rabbit anti-PAX6 (#901301; 1:1000; BioLegend, San Diego, Calif.), goat anti-biotinylated-OTX2 (#BAF1979; 1:500; R&D Systems), rabbit anti-Ki67 (#ab15580; 1:500; Abcam, Cambridge, Mass.), rabbit anti-TUJ1 (#T2200; 1:500; Sigma-Aldrich, St. Louis, Mo.), goat anti-biotinylated-NRL (#BAF2945; 1:500; R&D Systems), mouse anti-HuC/D (#A-21271; 1:500; Thermo Fisher Scientific, Waltham, Mass.), and rabbit anti-recoverin (#AB5585; 1:2000; EMD Millipore, Billerica, Mass.). To detect F-actin, eyecups were stained with Alexa Fluor 488 Phalloidin (#A12379; 1:500; Life Technologies). Primary antibodies were detected using fluorescently conjugated Alexa Fluor secondary antibodies (Life Technologies). Cell nuclei were counterstained using 4'6-diamidino-2-phenylindole. Sectioned eyecups were imaged using a Leica DM 2500 SPE confocal microscope (Leica Microsystems, Wetzler, Germany).

Results

Eleven families manifesting the clinical features of NCMD were studied, all but 1 of whom have been described phisms in the MCDR1 locus on chromosome 6, suggestive of a common founder,[45] whereas 5 others have been linked to MCDR1 but exhibit a different marker haplotype. The remaining family has been linked to the MCDR3 locus on chromosome 5.[22] DNA samples from 102 affected and 39 unaffected members of these families were available for this study. The family structures and specific individuals included in this study are shown in FIG. 4A-L.

Subject 7043 in family A has been observed by us for more than 30 years[43] and is an excellent example of the cardinal clinical features of NCMD. She was first seen at 2 years and 9 months of age and displayed a visual acuity of 20/40 in the right eye and 20/60 in the left eye with line pictures. Fundus examination revealed small areas of atrophy surrounded by drusen-like deposits in both eyes. A prism cover test revealed unmaintained fixation in the left eye, and a trial of part-time occlusion was begun. Two months later, her vision had improved to 20/40 in both eyes, and patching was discontinued. At age 6 years, her acuity had decreased slightly to 20/50 in both eyes. Two small red dots suggestive of hemorrhage were observed on the nasal edge of the atrophy in the left eye (FIG. 1A, B), but fluorescein angiography revealed no evidence of active neovascularization at that visit (FIG. 1C, D and FIG. 5). At age 8 years, her acuity remained 20/50 in both eyes and a new subretinal fibrotic scar was noted in the left eye, extending from 1 o'clock to 7 o'clock around the central patch of atrophy (FIG. 1E). Two years later, the acuity and fundus appearance were unchanged (FIG. 1F), but the following year, at age 11 years, the scar in the left eye had extended another 3 clock hours (FIG. 1G) with little change in acuity (20/50-2). When last seen at age 33 years, her visual acuity was 20/60-1 in the right eye and 20/70-1 in the left eye. The fundus appearance (FIG. 1H) was similar to that at her visit 22 years earlier. Optical coherence tomography of the left eye revealed an abrupt termination of the photoreceptors, retinal pigment epithelium, and choroid at the 1 edge of the atrophic lesion that was not distorted by the fibrotic scar (FIG. 1I).

Figure 2:
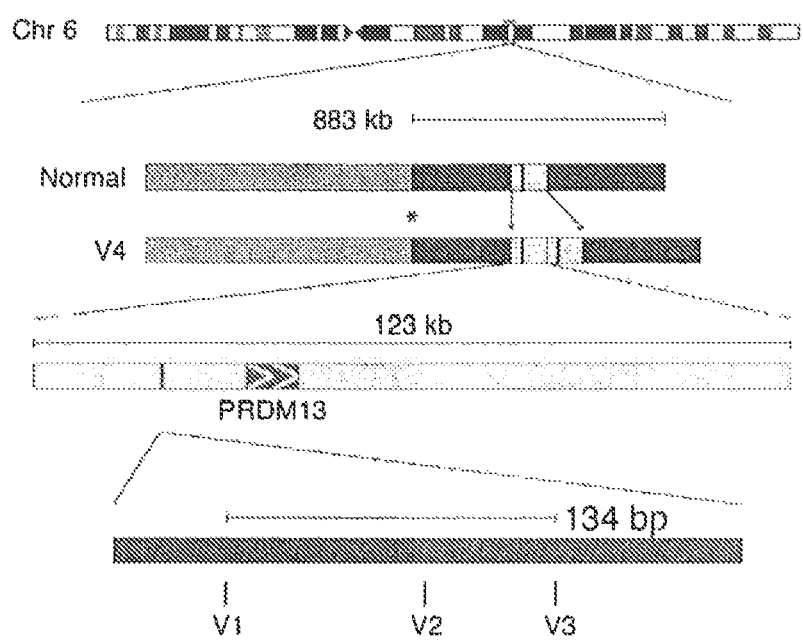
FIG. 2: Discovery of North Carolina macular dystrophy (NCMD)-causing variants in MCDR1. The critical region of MCDR1 was narrowed to 883 kb by Small et al. (recombinant denoted by asterisks here and in FIG. 4J, asterisk. Genome sequencing revealed 14 rare variants (violet vertical bars) across this region, 1 of which (V1) has never been observed in normal individuals. This novel variant falls within a DNase hypersensitivity site (pink) upstream of the PRDM13 gene (green) that was later found to include other rare variants in NCMD families (V2 and V3). In addition, a 123-kb tandem duplication containing the PRDM13 gene (yellow, V4) was discovered in 1 NCMD family. bp=base pairs.
Figure 3:
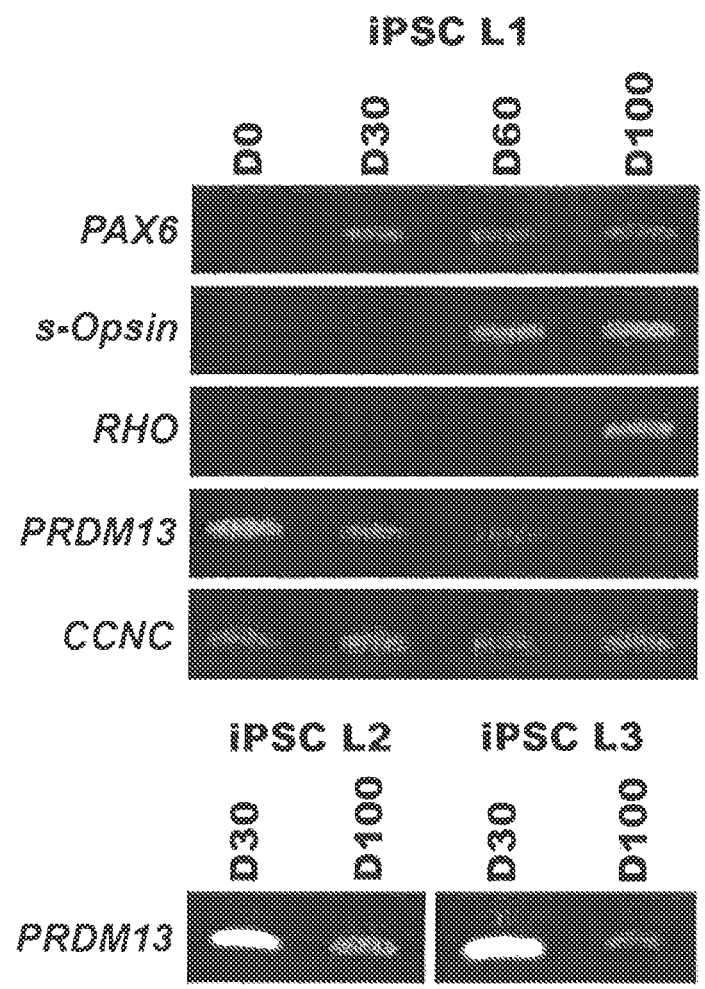
FIG. 3: Retinal expression of PRDM13 is developmentally regulated. Reverse transcription polymerase chain reaction analysis of induced pluripotent stem cells (iPSCs) after 0, 30, 60, and 100 days of retinal differentiation (D0, D30, D60, and D100, respectively) using primers targeted against the retinal lineage markers PAX6, s-Opsin, and Rhodopsin, and genes within the MCDR1 locus, PRDM13 and CCNC. As iPSCs progress from a pluripotent state to immature PAX6-expressing retinal progenitor cells to mature s-Opsin-expressing cone and rhodopsin-expressing rod photoreceptor cells, PRDM13 expression decreases (PRDM13 iPSC-L1, iPSC-L2, and iPSC-L3). iPSC-L1=control iPSC line 1; iPSC-L2=control iPSC line 2; iPSC-L3=control iPSC line 3.
Figure 4A:
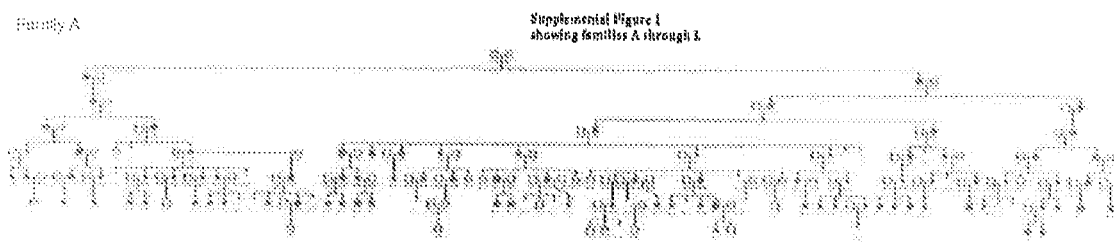
FIG. 4A-L: Pedigrees of families included in this study. Individuals from whom DNA was available in sufficient quantity and quality are indicated in green, individuals who were studied using next-generation sequencing are indicated in blue. The individual mark with the asterisk in Family K harbored the interval defining recombination.
Figure 4B:
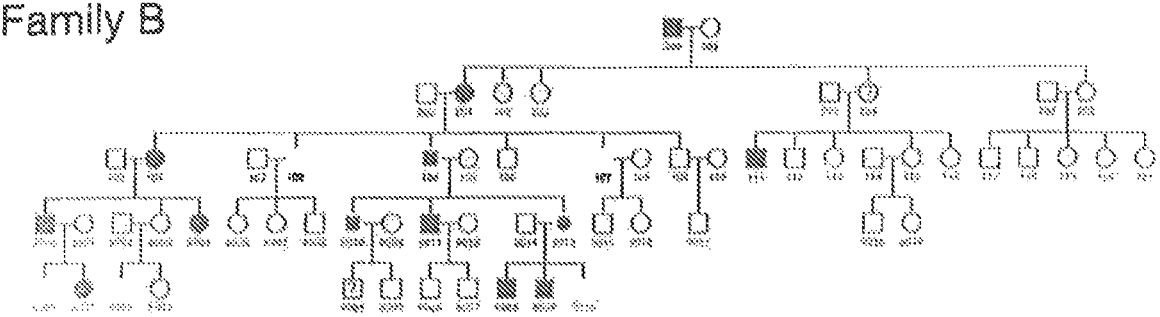
Figure 4C:
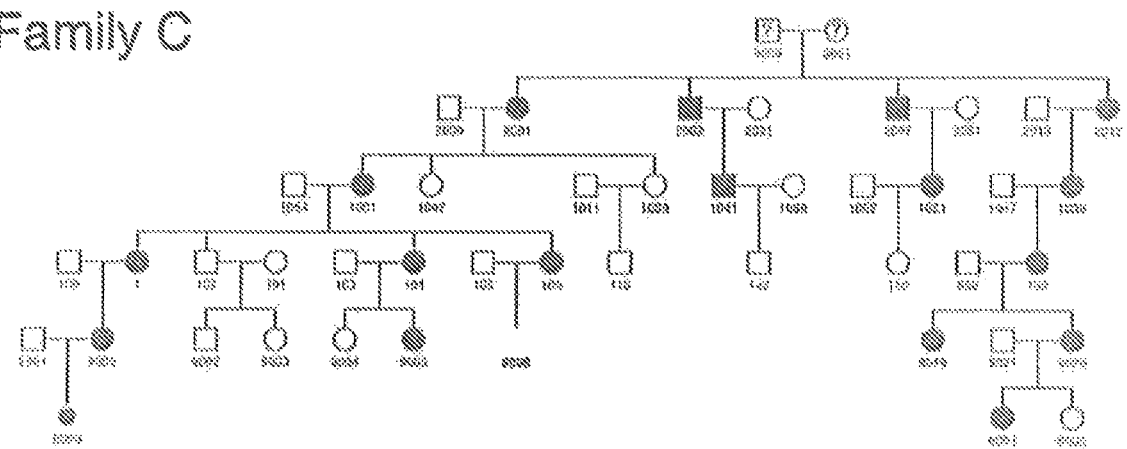
Figure 4D:
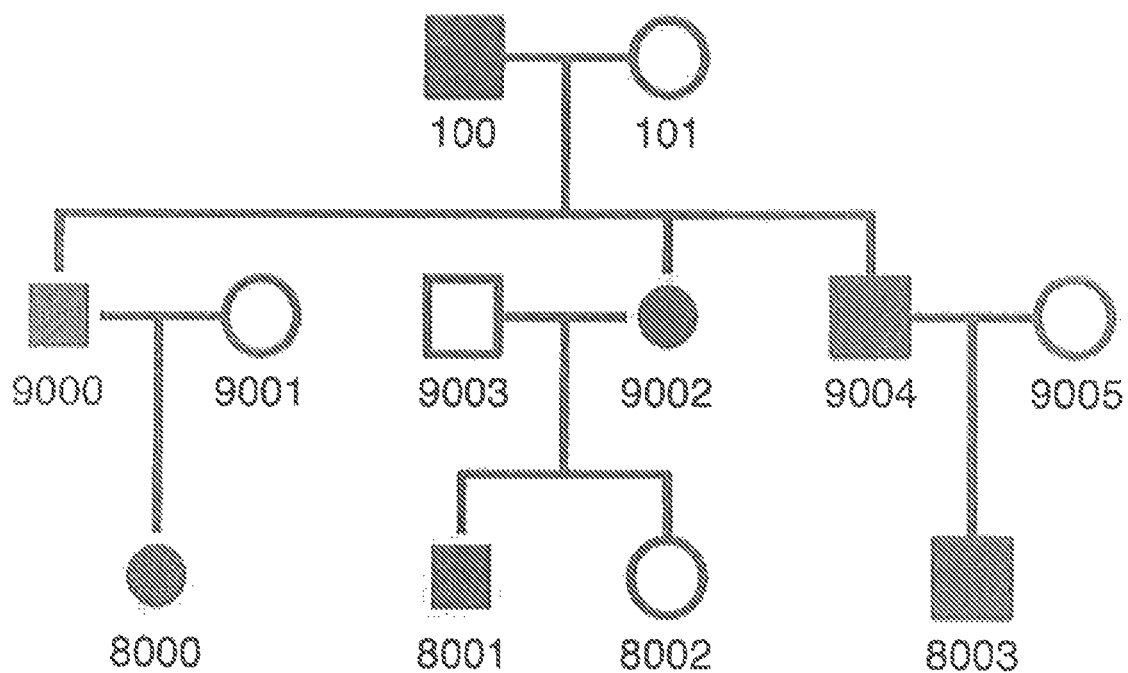
Figure 4E:
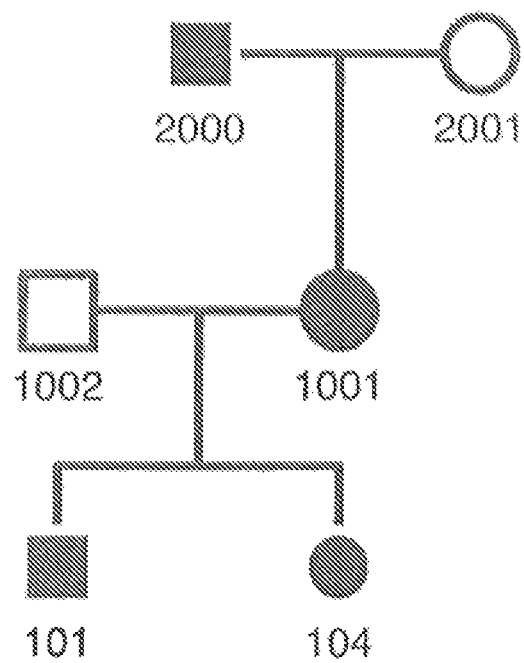
Figure 4F:
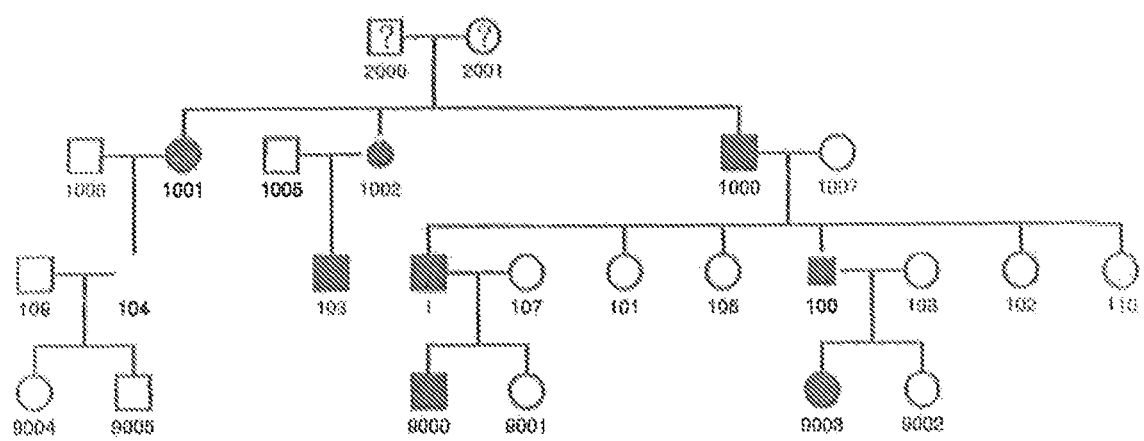
Figure 4G:
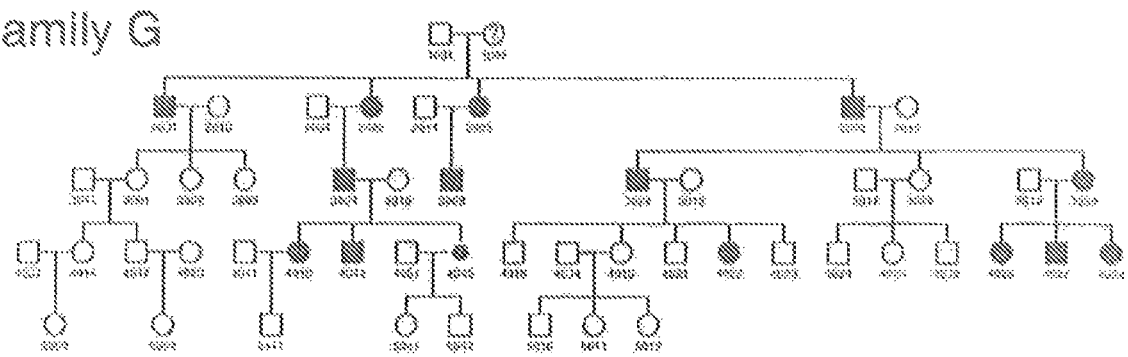
Figure 4H:
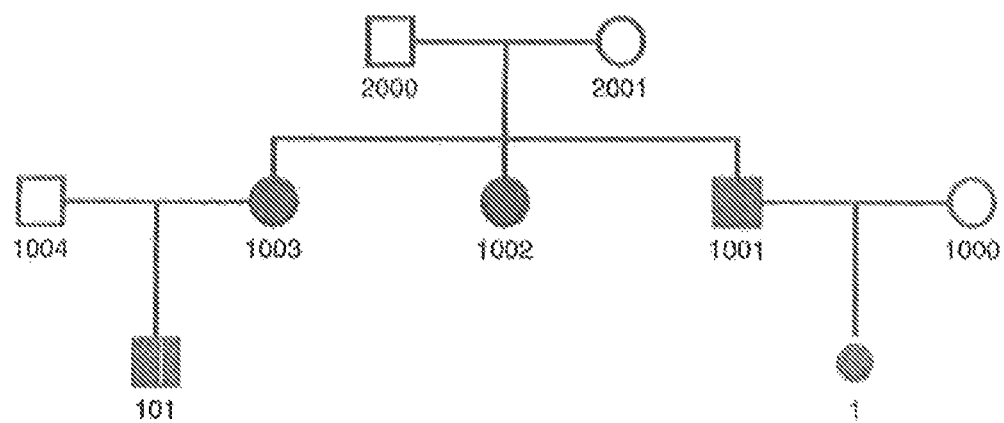
Figure 4I:
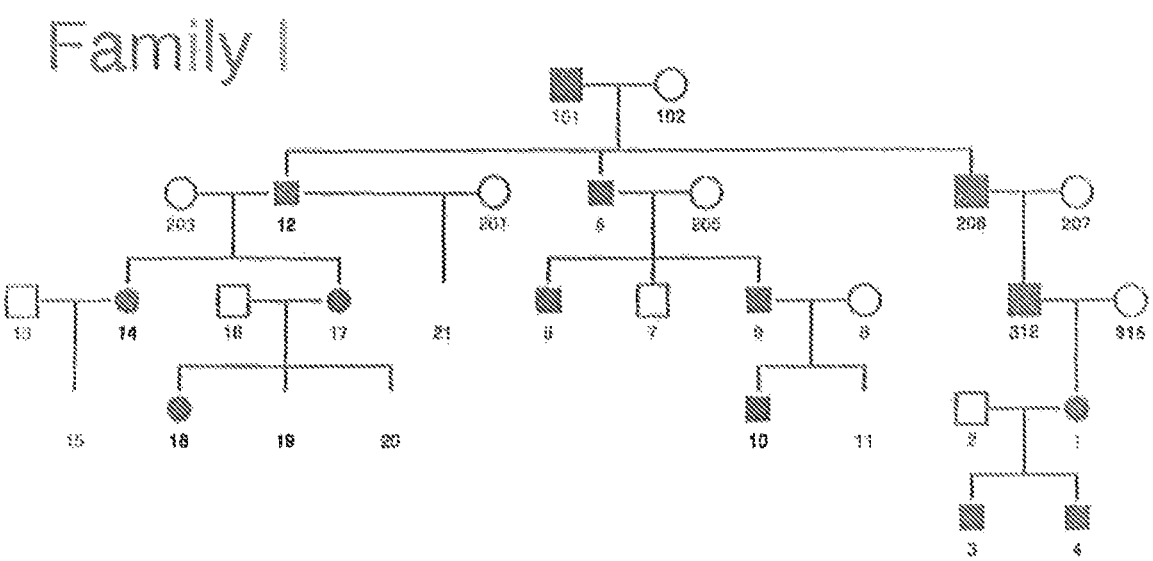
Figure 4J:
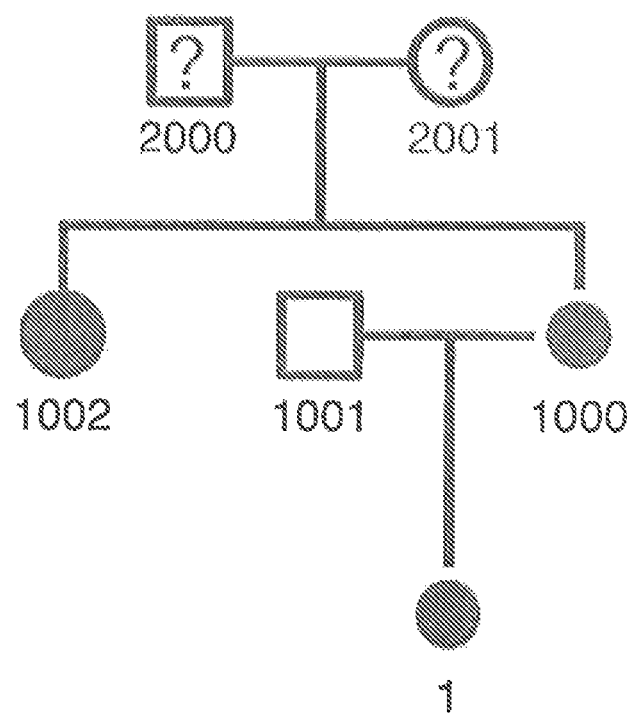
Figure 4K:
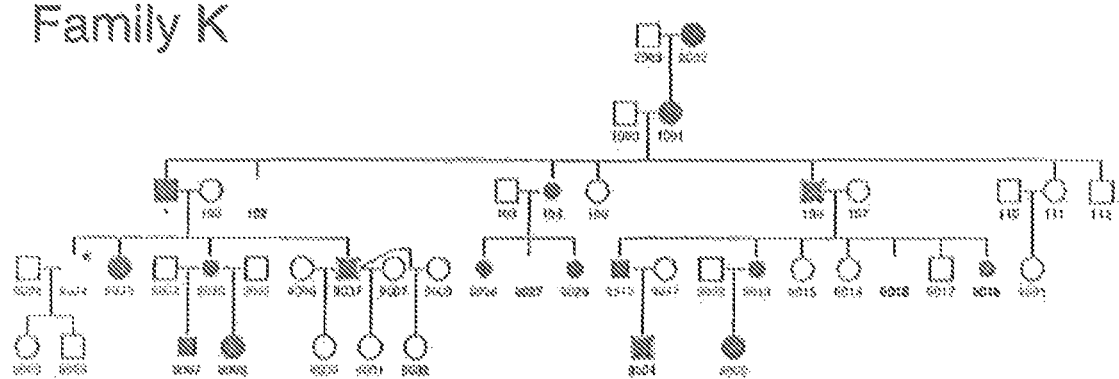
Figure 4L:
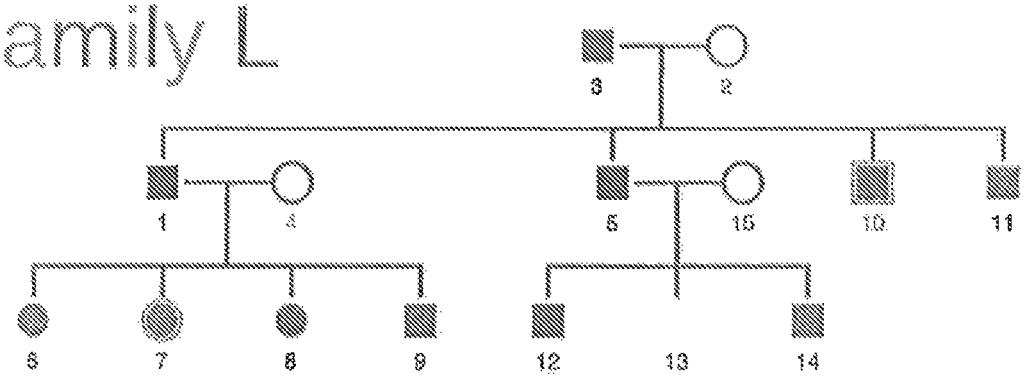

The original linkage of the NCMD phenotype to chromosome 6q[11] and the subsequent narrowing of the MCDR1 interval[24] depended heavily on families A and J. Detailed genotyping of additional members of these families revealed an unaffected recombinant individual (FIG. 4K) that narrowed the centromeric end of the interval to the genetic marker D6S 1717 (FIG. 2). A genomic fragment capture of the narrowed disease interval and next-generation sequencing were then performed in 1 unaffected and 2 affected members of family A. However, only 85% of the nucleotides in the disease interval were successfully sequenced in this experiment, and therefore 2 additional affected members of the same family were subjected to whole-genome sequencing. Analysis of the sequence data from these 4 affected individuals (noted in blue in FIG. 4A) revealed a haplotype of 14 rare variants that spanned 1 Mb of the disease-causing allele (FIG. 2). One of these variants (V1; Table 1) was absent from all published databases and 261 normal controls, but was found in all affected members of 5 of 10 additional NCMD kindreds (families B-F; FIG. 4) that were known or suspected to map to MCDR1. This variant lies in a DNase 1 hypersensitivity site (DHS) upstream of both the PRDM13 and CCNC genes (FIG. 2). Sanger sequencing of 1000 base pairs (bp) centered on V1 was performed in the probands of the remaining 5 NCMD families, and 2 additional novel single nucleotide variants (V2 in families G-I and V3 in family J; Table 1; FIG. 4) were identified within 134 bp of the location of V1 (FIG. 2). Whole-genome sequencing of an affected individual from the remaining MCDR1 family (family K; FIG. 4) was performed, and a 123-kb tandem duplication (V4; Table 1) containing the entire coding sequence of PRDM13 was identified (FIG. 2 and FIG. 6A). Collectively, V1 to V4 were present in 91 of 91 affected members of these 11 families, absent from 38 of 38 unaffected members, and absent from 261 unrelated control individuals (522 chromosomes). In addition, a review of the Database of Genome Variants[46] revealed no instances of duplication of the entire PRDM13 coding sequence in normal individuals.

Discussion

The technologic advancements that have occurred in the field of human genomics since the NCMD locus on chromosome 6 was first identified[11] have been breathtaking. Few investigators who studied inherited eye diseases in the 1990s would have imagined that in less than 25 years, whole-genome sequencing of individual patients would be so commonplace that the sequence of thousands of unrelated individuals would be freely available in public databases[30, 31, 32] and that the President of the United States would launch a precision medicine initiative based on these new molecular capabilities and data.[47] However, the most valuable data in both the original linkage study and the present study were not molecular; the most valuable data were the detailed clinical observations that allowed several families with a rare and unusual phenotype to be correctly separated from thousands of other members of hundreds of other families with similar diseases caused by genes at other loci.

Although counterintuitive to many people, it is a fact that as genomic tools become more powerful and less expensive, accurate and detailed clinical information become more necessary for the correct interpretation of the resulting molecular data. There are both quantitative and qualitative reasons for this. Now that tens of thousands of genes can be assessed in a single patient, there are tens of thousands of additional opportunities to observe a plausible disease-causing variant by chance than if one investigated only a single gene. By using clinical data to focus the hypothesis to just a few genes, one can overcome the large multiple measurements problem inherent in whole-genome data.

The qualitative reason that molecular data have become more difficult to interpret as they have become easier and less expensive to acquire is embodied in the difference between the coding and noncoding portions of genes. Coding sequences exist in groups of 3 nucleotides, known as codons, that each specify a single amino acid in the resulting proteins. The universality of the genetic code allows one to predict the structural effect of a given coding sequence mutation on the resulting protein with greater accuracy than one could if the same mutation occurred in the noncoding portion of a gene, where its effect would be tempered by the actions of DNA binding proteins, DNA methylation, non-coding RNA molecules, the proximity to coding sequences, and other factors that are incompletely understood at the present time.

There are 10 genes in the MCDR1 locus, and individuals from multiple unrelated kindreds affected with MCDR1-linked NCMD have been extensively screened for mutations in the coding sequences of these genes, with no plausible disease-causing variants identified. Therefore, we expected that NCMD-causing mutations would eventually be found in the noncoding portions of the MCDR1 locus, and we took advantage of 2 valuable resources and 1 genetic fact to detect these mutations among the many functionally neutral polymorphisms that exist in the noncoding sequences of all individuals: (1) multiple unrelated families exhibiting a classic NCMD phenotype, (2) public genome databases with sequences of thousands of individuals,[30, 31, 32] and (3) the fact that mutations that cause high-penetrance autosomal-dominant diseases should be no more common in the general population than the disease itself.

The data supporting the pathogenicity of V1-V4 are compelling. In family A, the original NCMD family and the largest one ascertained to date, V1 is the only nucleotide in the 883-kb MCDR1 locus that is absent from all public databases and therefore of similar population frequency to NCMD itself. This variant lies in a 255-bp region of DNase I hypersensitivity that is upstream of a gene encoding a retinal transcription factor, PRDM13 (See FIG. 8 for sequence of the DNase I hypersensitive site). It is noteworthy that PRDM13 is the only gene in the MCDR1 critical region that is solely expressed in the neural retina.[48, 49] DNase I hypersensitivity is an indicator of chromatin accessibility that is often associated with transcription factor binding sites.[50] V1 was later found in 5 independently ascertained NCMD kindreds, shown to segregate perfectly among 65 affected and 29 unaffected members of these 6 families, and shown to be absent from 261 unrelated individuals ascertained in Iowa. The latter individuals were sequenced just to make sure that there was not an artifactual gap in the public genome data. Conventional sequencing of this DHS in 5 V1-negative NCMD families revealed that 4 harbored point mutations (V2 and V3) within 134 bp of V1.

Whole-genome sequencing of the fifth V1-negative family revealed a tandem duplication containing the DHS and the entire coding sequence of PRDM13 (V4). V2 to V4 were found to segregate perfectly among the 26 affected and 9 unaffected members of these 5 families and were absent from all public databases and the 261 control individuals from Iowa.

Although the association between these variants and the disease phenotype is extraordinarily strong ($P<10^{-29}$, by Fisher exact test), the mechanism by which they cause disease is far from established. For example, the gene CCNC, which encodes a ubiquitous cell cycle controller, lies in the opposite orientation of PRDM13 on the opposite side of the DHS and thus could, in principle, also be affected by these mutations and therefore be involved in the pathogenesis of NCMD. One argument against CNCC as an NCMD gene, in addition to its ubiquitous expression, is the configuration of the DHSs in the tandem duplication of family K. The entire coding region of PRDM13 is duplicated in this mutation, and both DHSs are immediately adjacent to a PRDM13 gene. In contrast, only 1 of the DHSs is adjacent to the unduplicated CCNC gene (FIG. 7A-B)

The observation that NCMD is a developmental abnormality is also consistent with PRDM13 being the responsible gene. PRDM13 is a member of a large family of "helix-loop-helix" DNA-binding proteins that play key roles in controlling gene expression during development.[51] Because the formation of the macula is accompanied by differential expression of an array of genes involved in axon guidance and inhibition of angiogenesis,[52] this process likely relies on a precise interaction between transcription factors (like PRDM13) and their target genes. Thus, a change in the abundance of a transcription factor due to mutations in its own regulatory regions could plausibly lead to impaired cell fate specifications in the developing macula. Therefore, it is notable that PRDM13 are proteins with important roles in regulating gene expression.

One of the great advantages of iPSCs is their ability to differentiate ex vivo into any cell type of the 3 embryonic germ layers. For many organ systems, iPSC differentiation faithfully recapitulates the various cell fate decisions made during embryonic development.[39, 53, 54, 55, 56] Being able to obtain embryonic tissue from adult somatic cells affords researchers with the ability to determine if and when in cellular development specific genes are expressed. In this study, human iPSC-derived retinal tissue was used to demonstrate that PRDM13 is developmentally regulated while other genes in the MCDR1 locus (i.e., CCNC) are not. To demonstrate this finding in the absence of the pluripotent stem cell technology, one would have to obtain retinal tissue from human fetuses at different points in development, an approach that would be logistically difficult and raise serious ethical concerns. The capability of iPSCs to generate otherwise inaccessible tissues such as the retina also gives researchers the ability to investigate the pathophysiologic effect of newly identified gene defects on cell health and function. This will be especially useful in the modern gene-sequencing era when trying to determine the mechanistic effects of noncoding genetic variants such as those identified in this study. In future studies, it will be interesting to generate retinal tissue from patients with each of the mutations described in this study and to determine their effect on gene expression, as well as cellular differentiation, maturation, health, and function.

Unlike MCDR1, no additional mutations have been identified in different MCDR3 families to corroborate this finding and to narrow the mechanistic possibilities. Also unlike MCDR1, PRDM13 exhibits dramatic expression differences in the first 100 days of retinal development. Future experiments with retinal cells generated from patients with NCMD themselves will likely significantly clarify the mechanism of both MCDR loci.

A practical outcome of this work is that one can detect every mutation reported in this article using only 3 polymerase chain reaction-based sequencing reactions (Supplemental Table 1). The availability of a simple genetic test for this disease will likely result in the diagnosis of many additional individuals, which not only will allow physicians to provide more accurate genetic and prognostic information than was possible before but also will likely accelerate the discovery of additional disease-causing variants and additional clinical manifestations of the known mutations. Both of these will help unravel the precise mechanisms through which these loci contribute to the formation of the normal macula.

In conclusion, we identified 5 rare mutations that each are capable of arresting the development of the human macula. Four of these strongly implicate the involvement of the gene PRDM13 in macular development, whereas the pathophysiologic mechanism of the fifth remains unknown.

Supplemental Data

Supplemental Table 1 Oligonucleotide Primers

| Primer Name | Type | Sequence Description | Forward Sequence | Reverse Sequence |
| --- | --- | --- | --- | --- |
| PRDM13-DHS_1 | S | chr6_100040343-100040606 | GCATTCCCTAAAGCACTTGACC (SEQ ID NO.: 5) | GATAGCTACCCCTCCTCTGAATG (SEQ ID NO.: 6) |
| PRDM13-DHS_2 | S | chr6_100040524-100040879 | CTGATCATTTGAATCAAGGCAG (SEQ ID NO.: 7) | CAGCACTTGCACATTTGTGTC (SEQ ID NO.: 8) |
| PRDM13-DHS_3* | S | chr6_100040803-100041001 | GAGAAGACTAGATCAGGCTTCTTC (SEQ ID NO.: 9) | CTCTCATTCTCTGATTTTTAC (SEQ ID NO.: 10) |
| PRDM13-DHS_5 | S | chr6_100041063-100041470 | CACTGGAAAAATTATGTGGAAATC (SEQ ID NO.: 11) | GAGTAATTAATGAAGTTGACAAGTTG (SEQ ID NO.: 12) |
| PRDM13_Duplication* | J | chr6_Junction Fragment | GATAAATCATATCTTAGACCGC (SEQ ID NO.: 13) | CTCATGCCTATAATCCCAGCAC (SEQ ID NO.: 14) |
| IRX1_Duplication* | J | chr5_Junction Fragment | GTTTTCACGAAAGTGCAAAGG (SEQ ID NO.: 15) | GGGGTGGAAGAGAAGAGAGG (SEQ ID NO.: 16) |

Supplemental Table 1_Oligonucleotide Primers

| Primer Name | Type | Sequence Description | Forward Sequence | Reverse Sequence |
|---|---|---|---|---|
| PRDM13 | R | Exon 3 to Exon 4 | GGAGGAGCTGACAGTGTGGT (SEQ ID NO.: 17) | AAACGTCCTCCAGCAGTACCAG (SEQ ID NO.: 18) |
| IRX1 | R | Exon 3 to Exon 4 | CAGCAGTTAAAGTCGCCCTT (SEQ ID NO.: 19) | AAAAGTAAAAGAAGACCCTTAA (SEQ ID NO.: 20) |
| CCNC | R | Exon 8 to Exon 9 | CTTGATAGTGTATCATCCTTATA (SEQ ID NO.: 21) | TCATTCACTATCCTCCATGCAAGG (SEQ ID NO.: 22) |
| PAX6 | R | Exon 5 to Exon 7 | CCGGCAGAAGATTGTAGAGC (SEQ ID NO.: 23) | GCCCGTTCAACATCCTTAGT (SEQ ID NO.: 24) |
| RHO | R | Exon 2 to Exon 5 | GGGAGAACCATGCCATCAT (SEQ ID NO.: 25) | TCGTCTCCGTCTTGGACAC (SEQ ID NO.: 26) |
| S-Opsin | R | Exon 1 to Exon 2 | CGCCAGCTGTGAACGGATACT (SEQ ID NO.: 27) | CCAATACCAATGGTCCAGGT (SEQ ID NO.: 28) |

*Primers used to detect variants V1-V5
Oligo Type: S = sequencing amplification of genomic DNA, J = amplification spanning the 5' junction fragment, R = RT-PCR amplification from RNA

REFERENCES

1. Friedman D S, O'Colmain B J, Muñoz B, et al. Prevalence of age-related macular degeneration in the United States. Arch Ophthalmol 2004; 122:564-72.
2. Klein R, Klein B E, Cruickshanks K J. The prevalence of age related maculopathy by geographic region and ethnicity. Prog Retin Eye Res 1999; 18:371-89.
3. Wong T Y, Wong T, Chakravarthy U, et al. The natural history and prognosis of neovascular age-related macular degeneration: a systematic review of the literature and meta-analysis. Ophthalmology 2008; 115:116-26.
4. Wong W L, Su X, Li X, et al. Global prevalence of age-related macular degeneration and disease burden projection for 2020 and 2040: a systematic review and meta-analysis. Lancet Glob Health 2014; 2:e106-16.
5. Rosenfeld P J, Brown D M, Heier J S, et al. Ranibizumab for neovascular age-related macular degeneration. N Engl J Med 2006; 355:1419-31.
6. Rosenfeld P J, Moshfeghi A A, Puliafito C A. Optical coherence tomography findings after an intravitreal injection of bevacizumab (Avastin) for neovascular age-related macular degeneration. Ophthalmic Surg Lasers Imaging 2005; 36: 331-5.
7. CATT Research Group, Martin D F, Maguire M G, et al. Ranibizumab and bevacizumab for neovascular age related macular degeneration. N Engl J Med 2011; 364: 1897-908.
8. Bressler N M, Doan Q V, Varma R, et al. Estimated cases of legal blindness and visual impairment avoided using ranibizumab for choroidal neovascularization: non-Hispanic white population in the United States with age-related macular degeneration. Arch Ophthalmol 2011; 129:709-17.
9. Tucker B A, Mullins R F, Streb L M, et al. Patient-specific iPSC-derived photoreceptor precursor cells as a means to investigate retinitis pigmentosa. Elife 2013; 2:e00824.
10. Tucker B A, Park I H, Qi S D, et al. Transplantation of adult mouse iPS cell-derived photoreceptor precursors restores retinal structure and function in degenerative mice. PLoS One 2011; 6:e18992.
11. Small K W, Weber J L, Roses A, et al. North Carolina macular degeneration is assigned to chromosome 6. Genomics 1992; 13: 681-5.
12. Lefler W H, Wadsworth J A, Sidbury J B. Hereditary macular degeneration and amino-aciduria. Am J Ophthalmol 1971; 71: 224-30.
13. Frank H R, Landers M B, Williams R J, Sidbury J B. A new dominant progressive foveal degeneration. Am J Ophthalmol 1974; 78:903-16.
14. Small K W. North Carolina macular degeneration, revisited. Ophthalmology 1989; 96:1747-54.
15. Pauleikhoff D, Sauer C G, Müller C R, et al. Clinical and genetic evidence for autosomal dominant North Carolina macular degeneration in a German family. Am J Ophthalmol 1997; 124: 412-5.
16. Small K W, Puech B, Mullen L, Yelchits S. North Carolina macular degeneration phenotype in France maps to the MCDR1 locus. Mol Vis 1997; 3:1.
17. Small K W, Garcia C A, Gallardo G, et al. North Carolina macular degeneration (MCDR1) in Texas. Retina 1998; 18:448-52.
18. Rohrschneider K, Blankenagel A, Kruse F E, et al. Macular function testing in a German pedigree with North Carolina macular degeneration. Retina 1998; 18:453-9.
19. Rabb M F, Mullen L, Yelchits S, et al. A North Carolina macular degeneration phenotype in a Belizean family maps to the MCDR1 locus. Am J Ophthalmol 1998; 125:502-8.
20. Reichel M B, Kelsell R E, Fan J, et al. Phenotype of a British North Carolina macular degeneration family linked to chromosome 6q. Br J Ophthalmol 1998; 82:1162-8.
21. Michaelides M, Johnson S, Tekriwal A K, et al. An early-onset autosomal dominant macular degeneration (MCDR3) resembling North Carolina macular degeneration maps to chromosome 5. Invest Ophthalmol Vis Sci 2003; 44:2178-83.
22. Rosenberg T, Roos B, Johnsen T, et al. Clinical and genetic characterization of a Danish family with North Carolina macular degeneration. Mol Vis 2010; 16:2659-68.

23. Sauer C G, Schworm H D, Ulbig M, et al. An ancestral core haplotype defines the critical region harbouring the North Carolina macular degeneration gene (MCDR1). J Med Genet 1997; 34:961-6.
24. Small K W, Udar N, Yelchits S, et al. North Carolina macular degeneration (MCDR1) locus: a fine resolution genetic map and haplotype analysis. Mol Vis 1999; 5:38.
25. Yang Z, Tong Z, Chorich U, et al. Clinical characterization and genetic mapping of North Carolina macular degeneration. Vision Res 2008; 48:470-7.
26. Braun T A, Mullins R F, Wagner A H, et al. Non-exomic and synonymous variants in ABCA4 are an important cause of Stargardt disease. Hum Mol Genet 2013; 22: 5136-45.
27. Tucker B A, Scheetz T E, Mullins R F, et al. Exome sequencing and analysis of induced pluripotent stem cells identify the cilia-related gene male germ cell-associated kinase (MAK) as a cause of retinitis pigmentosa. Proc Natl Acad Sci USA 2011; 108:E569-76.
28. Li H, Durbin R. Fast and accurate long-read alignment with Burrows-Wheeler transform. Bioinformatics 2010; 26:589-95.
29. McKenna A, Hanna M, Banks E, et al. The Genome Analysis Toolkit: a MapReduce framework for analyzing next generation DNA sequencing data. Genome Res 2010; 20:1297-303.
30. Exome Aggregation Consortium (ExAC). Available at: http://exac.broadinstitute.org. Accessed Dec. 9, 2014.
31. Exome Variant Server. NHLBI Exome Sequencing Project (ESP) Available at: http://evs.gs.washington.edu/EVS/. Accessed Jun. 27, 2012.
32. 1000 Genomes Project Consortium. A map of human genome variation from population-scale sequencing. Nature 2010; 467: 1061-73.
33. Ye K, Schulz M H, Long Q, et al. Pindel: a pattern growth approach to detect break points of large deletions and medium sized insertions from paired-end short reads. Bioinformatics 2009; 25:2865-71.
34. Thorvaldsdottir H, Robinson J T, Mesirov J P. Integrative Genomics Viewer (IGV): high-performance genomics data visualization and exploration. Brief Bioinform 2013; 14:178-92.
35. Krumm N, Sudmant P H, Ko A, et al. Copy number variation detection and genotyping from exome sequence data. Genome Res 2012; 22:1525-32.
36. Mykytyn K, Nishimura D Y, Searby C C, et al. Identification of the gene (BBS 1) most commonly involved in Bardet-Biedl syndrome, a complex human obesity syndrome. Nat Genet 2002; 31:435-8.
37. Tucker B A, Anfinson K R, Mullins R F, et al. Use of a synthetic xeno-free culture substrate for induced pluripotent stem cell induction and retinal differentiation. Stem Cells Transl Med 2013; 2:16-24.
38. Burnight E R, Wiley L A, Drack A V, et al. CEP290 gene transfer rescues Leber congenital amaurosis cellular phenotype. Gene Ther 2014; 21:662-72.
39. Eiraku M, Takata N, Ishibashi H, et al. Self-organizing optic cup morphogenesis in three-dimensional culture. Nature 2011; 472:51-6.
40. Fetkenhour C L, Gurney N, Dobbie J G, Choromokos E. Central areolar pigment epithelial degeneration. Am J Ophthalmol 1976; 81:745-53.
41. Hermsen V M, Judisch G F. Central areolar pigment epithelial degeneration. Ophthalmologica 1984; 189:69-72.
42. Small K W, Killian J, McLean W C. North Carolina's dominant progressive foveal degeneration: how progressive is it? Br J Ophthalmol 1991; 75:401-6.
43. Small K W, Hermsen V, Gurney N, et al. North Carolina macular degeneration and central areolar pigment epithelial degeneration. One family, one disease. Arch Ophthalmol 1992; 110:515-8.
44. Keithahn M A, Huang M, Keltner J L, et al. The variable expressivity of a family with central areolar pigment epithelial degeneration. Ophthalmology 1996; 103:406-15.
45. Small K W. North Carolina macular degeneration: clinical features, genealogy, and genetic linkage analysis. Trans Am Ophthalmol Soc 1998; 96:925-61.
46. MacDonald J R, Ziman R, Yuen R K C, et al. The Database of Genomic Variants: a curated collection of structural variation in the human genome. Nucleic Acids Res 2014; 42:D986-92.
47. Collins F S, Varmus H. A new initiative on precision medicine. N Engl J Med 2015; 372:793-5.
48. Whitmore S S, Wagner A H, DeLuca A P, et al. Transcriptomic analysis across nasal, temporal, and macular regions of human neural retina and RPE/choroid by RNA-Seq. Exp Eye Res 20141-14.
49. Melé M, Ferreira P G, Reverter F, et al. Human genomics. The human transcriptome across tissues and individuals. Science 2015; 348:660-5.
50. Thurman R E, Rynes E, Humbert R, et al. The accessible chromatin landscape of the human genome. Nature 2012; 489: 75-82.
51. Fog C K, Galli G G, Lund A H. PRDM proteins: important players in differentiation and disease. Bioessays 2012; 34:50-60.
52. Kozulin P, Natoli R, O'Brien K M B, et al. Differential expression of anti-angiogenic factors and guidance genes in the developing macula. Mol Vis 2009; 15:45-59.
53. Lancaster M A, Renner M, Martin C-A, et al. Cerebral organoids model human brain development and microcephaly. Nature 2013; 501:373-9.
54. Spence J R, Mayhew C N, Rankin S A, et al. Directed differentiation of human pluripotent stem cells into intestinal tissue in vitro. Nature 2011; 470:105-9.
55. Xia Y, Sancho-Martinez I, Nivet E, et al. The generation of kidney organoids by differentiation of human pluripotent cells to ureteric bud progenitor-like cells. Nat Protoc 2014; 9: 2693-704.
56. Zhong X, Gutierrez C, Xue T, et al. Generation of three dimensional retinal tissue with functional photoreceptors from human iPSCs. Nat Commun 2014; 5:4047.
57. Tena J J, Alonso M E, la Calle-Mustienes de E, et al. An evolutionarily conserved three-dimensional structure in the vertebrate Irx clusters facilitates enhancer sharing and co-regulation. Nat Commun 2011; 2:310.

What is claimed is:

1. A method for diagnosing North Carolina Macular Degeneration and inhibiting macular degeneration in a subject so diagnosed comprising:
   a) obtaining a biological sample from the subject;
   b) determining presence of a mutation in a nuclease hypersensitive region or a transcriptional regulatory region of a retinal transcription factor gene, PRDM13 gene in the sample, wherein the mutation is selected from the group of: a guanine to thymidine change at position 21 of SEQ ID NO: 31, a guanine to cytosine change at position 21 of SEQ ID NO: 33, a cytosine to thymine change at position 21 of SEQ ID NO: 35, a 123-kb tandem duplication of chromosomal DNA on human chromosome 6 at location chr6:100020205-100143306, and an insertion of a 22-bp DNA sequence, ATTTACTTTATGTGTTTGCATG (SEQ ID NO:1), between duplicated chr6:100020205-100143306 DNA on human chromosome 6; wherein presence of any said mutation is associated with North Carolina Macular Degeneration, thereby diagnosing North Carolina Macular Degeneration in the subject; and
   c) administering in an eye of the subject so diagnosed a retinal cell, progenitor cell or a pluripotent stem cell lacking the mutation in a sufficient amount and under suitable conditions so that the cells form part or all of a macula lutea in the subject, thereby inhibiting macular degeneration in the subject.

2. The method of claim 1, wherein the biological sample comprises a cell from said subject.

3. The method of claim 1, wherein the biological sample comprises nucleic acid from said subject.

4. The method of claim 3, wherein the nucleic acid comprises DNA, RNA or a combination thereof.

5. The method of claim 1, wherein the retinal cell is selected from the set of a photoreceptor cell, a non-photoreceptor neuron and a glial cell.

6. The method of claim 5, wherein the photoreceptor cell is selected from the set of a rod photoreceptor cell, a cone photoreceptor cell and a photosensitive retinal ganglion cell.

7. The method of any of claim 1, wherein the pluripotent stem cell is an induced pluripotent stem cell.

8. The method of any of claim 1, wherein the retinal cell, the progenitor cell or the pluripotent stem cell is derived from said subject.

9. The method of any of claim 1, wherein the retinal cell, the progenitor cell or the pluripotent stem cell is derived from said subject and is genetically altered.

* * * * *